United States Patent
Euliano et al.

(10) Patent No.: US 10,292,642 B2
(45) Date of Patent: *May 21, 2019

(54) ELECTRONIC MEDICATION COMPLIANCE MONITORING SYSTEM AND ASSOCIATED METHODS

(71) Applicant: etectRx, Inc., Orlando, FL (US)

(72) Inventors: Neil R. Euliano, Gainesville, FL (US);
Brent A. Myers, Palm Bay, FL (US);
Jose C. Principe, Gainesville, FL (US);
Venkata V. Meka, Oakland, CA (US);
Glen Flores, Gainesville, FL (US)

(73) Assignee: etectRx, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/687,212

(22) Filed: Aug. 25, 2017

(65) Prior Publication Data

US 2018/0132784 A1     May 17, 2018

Related U.S. Application Data

(63) Continuation of application No. 14/726,899, filed on Jun. 1, 2015, now Pat. No. 9,743,880, which is a continuation of application No. 12/881,572, filed on Sep. 14, 2010, now Pat. No. 9,047,746, which is a
(Continued)

(51) Int. Cl.
| | |
|---|---|
| *G08B 23/00* | (2006.01) |
| *A61B 5/00* | (2006.01) |
| *A61B 5/07* | (2006.01) |
| *A61B 5/145* | (2006.01) |
| *G06F 19/00* | (2018.01) |

(Continued)

(52) U.S. Cl.
CPC ............ *A61B 5/4833* (2013.01); *A61B 5/065* (2013.01); *A61B 5/07* (2013.01); *A61B 5/073* (2013.01); *A61B 5/14539* (2013.01); *A61B 5/42* (2013.01); *G06F 19/00* (2013.01); *G06F 19/3456* (2013.01); *G08B 23/00* (2013.01); *A61B 5/0421* (2013.01); *A61B 2560/0209* (2013.01); *A61B 2560/0214* (2013.01); *A61M 2205/3592* (2013.01); *G06F 19/3462* (2013.01)

(58) Field of Classification Search
CPC .. A61B 5/06; A61B 5/061; A61B 5/07; A61B 5/073; A61B 5/0031; A61B 5/42; A61B 5/14539; A61B 5/4833; A61K 9/0097; A61J 2200/30
USPC ..... 340/539.1, 539.11, 539.12, 572.1, 573.1, 340/286.07; 600/300, 301, 302; 128/903, 904, 204.18
See application file for complete search history.

(56) References Cited

U.S. PATENT DOCUMENTS

| | | | | |
|---|---|---|---|---|
| 7,005,986 B2 * | 2/2006 | Parks, III | ............... | G08B 21/20 |
| | | | | 128/903 |
| 7,253,716 B2 * | 8/2007 | Lovoi | .................... | A61J 3/007 |
| | | | | 340/10.1 |

(Continued)

*Primary Examiner* — Hung T Nguyen
(74) *Attorney, Agent, or Firm* — Bass, Berry & Sims PLC

(57) ABSTRACT

A system and method for monitoring a patient's compliance with a medication regimen includes an electronic tag integral with or attached to a medicine delivery device such as a capsule, the tag having an antenna and a receiver/transmitter, the system also including a reader positioned externally for detecting the presence and location of the delivery device in the patient.

20 Claims, 24 Drawing Sheets

FIG. 1

Related U.S. Application Data continuation-in-part of application No. 11/458,815, filed on Jul. 20, 2006, now Pat. No. 7,796,043.

(60) Provisional application No. 60/700,963, filed on Jul. 20, 2005, provisional application No. 60/734,483, filed on Nov. 8, 2005, provisional application No. 60/746,935, filed on May 10, 2006.

(51) Int. Cl.
*A61B 5/06* (2006.01)
*A61B 5/042* (2006.01)

(56) References Cited

U.S. PATENT DOCUMENTS

| | | | | |
|---|---|---|---|---|
| 7,504,954 B2 * | 3/2009 | Spaeder | ............... | A61K 9/0097 128/204.18 |
| 8,038,599 B2 * | 10/2011 | Kimoto | ............. | A61B 1/00016 600/118 |
| 2005/0285732 A1 * | 12/2005 | Sengupta | ............ | G06F 19/3462 340/539.12 |

* cited by examiner

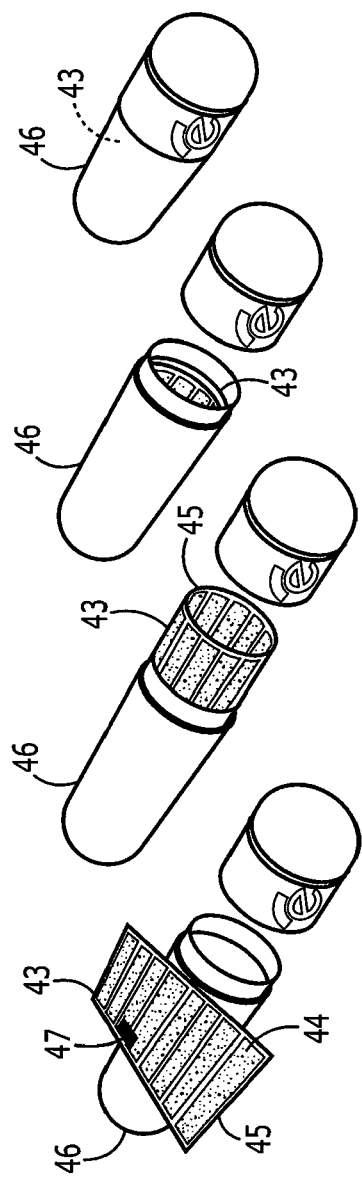
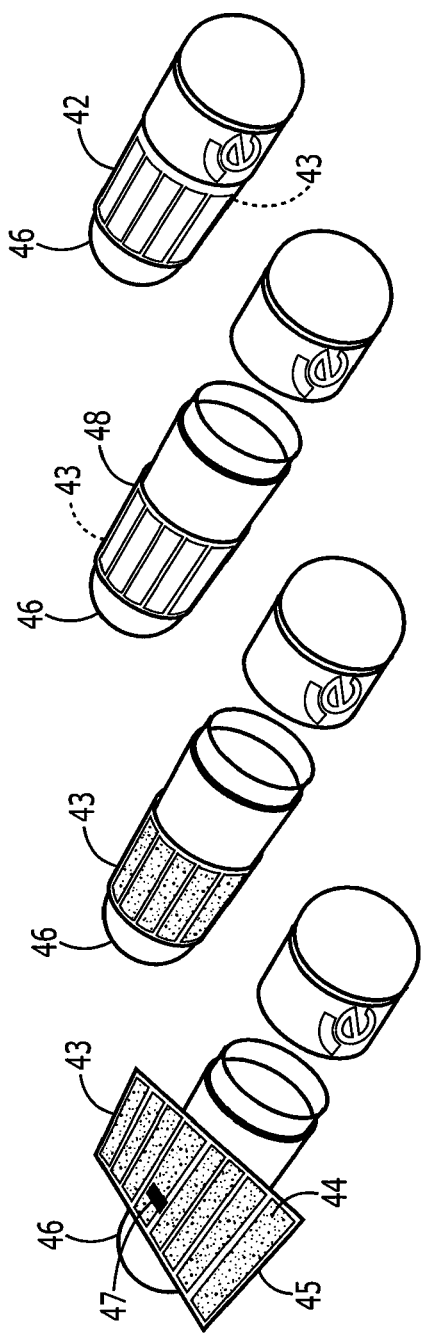
FIG. 5A
FIG. 5B

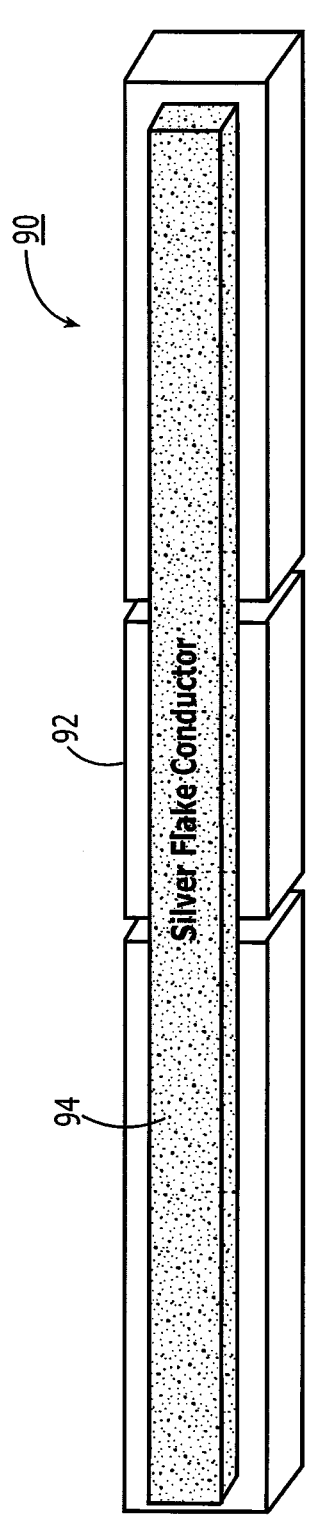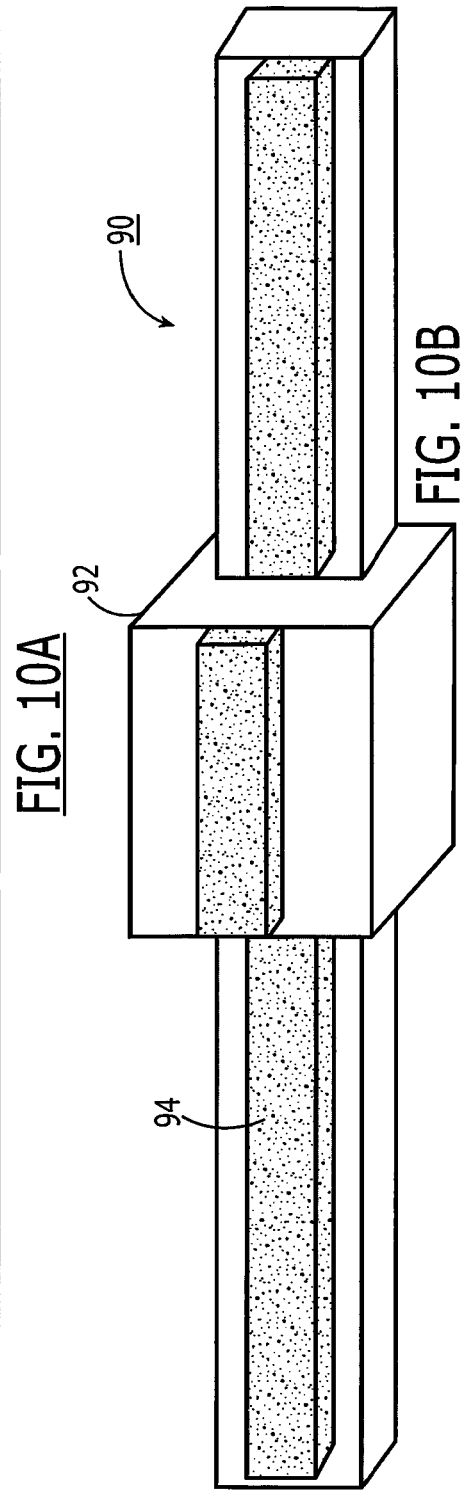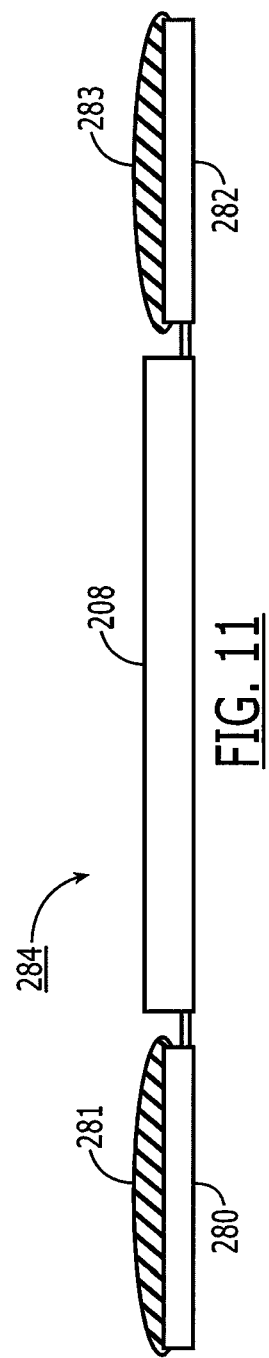

Results
| Electrode formation | 20 kOhm load | | | | | | 1 kOhm load | |
|---|---|---|---|---|---|---|---|---|
| time | 5 s | 5 s | 10 s | 10 s | 15 s | 15 s | 5 s | 10 s |
| Run | 1 | 2 | 1 | 2 | 1 | 2 | 1 | 2 |
| Test solution / Time (s) | Voltage (V) | | | | | | | |
| H2SO4   0 | 1.400 | 1.402 | 1.449 | 1.426 | 1.423 | 1.422 | 1.406 | 1.440 |
| 30 | 1.209 | 1.180 | 1.368 | 1.419 | 1.389 | 1.415 | 0.980 | 1.403 |
| 60 | 1.120 | 1.108 | 1.339 | 1.404 | 1.398 | 1.406 | 1.004 | 1.383 |
| 90 | 1.099 | 1.090 | 1.320 | 1.398 | 1.411 | 1.405 | 1.012 | 1.376 |
| 120 | 1.086 | 1.076 | 1.280 | 1.391 | 1.423 | 1.400 | 1.013 | 1.374 |
| HCl    0 | 1.017 | 1.051 | 1.090 | 1.323 | 1.274 | 1.218 | 1.016 | 1.330 |
| 30 | 1.050 | 1.029 | 1.052 | 1.097 | 1.053 | 0.994 | 1.007 | 1.013 |
| 60 | 1.043 | 1.023 | 1.048 | 1.037 | 1.052 | 0.990 | 1.004 | 1.008 |
| 90 | 1.035 | 1.018 | 1.045 | 1.030 | 1.045 | 0.984 | 1.001 | 1.001 |
| 120 | 1.024 | 1.014 | 1.043 | 1.026 | 1.042 | 0.983 | 0.998 | 0.996 |
| 15* |  |  |  |  | 1.070 | 1.015 |  | 1.039 |
*15 s reading taken to show that the drop is dramatic within the first 15 s and not just 30 s
FIG. 12A
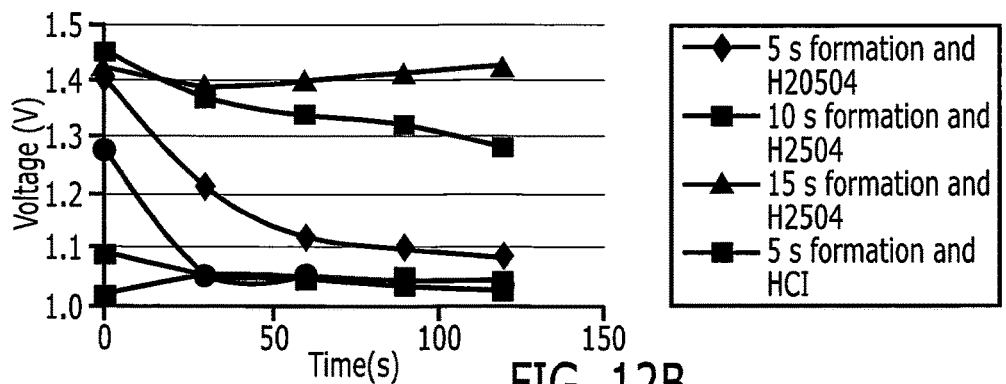
FIG. 12B
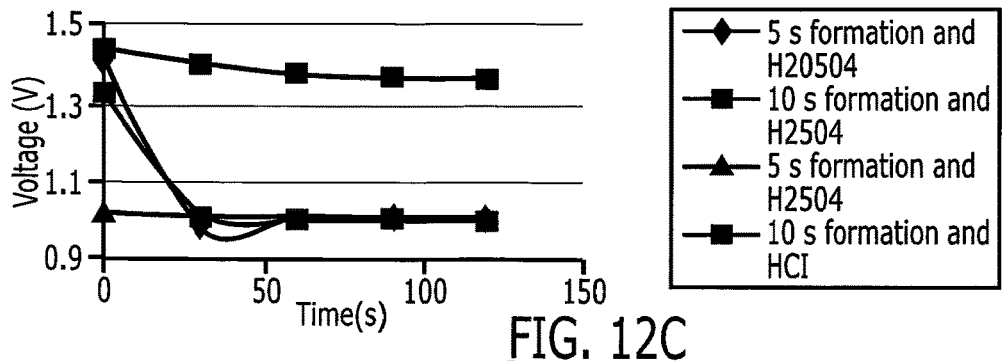
FIG. 12C

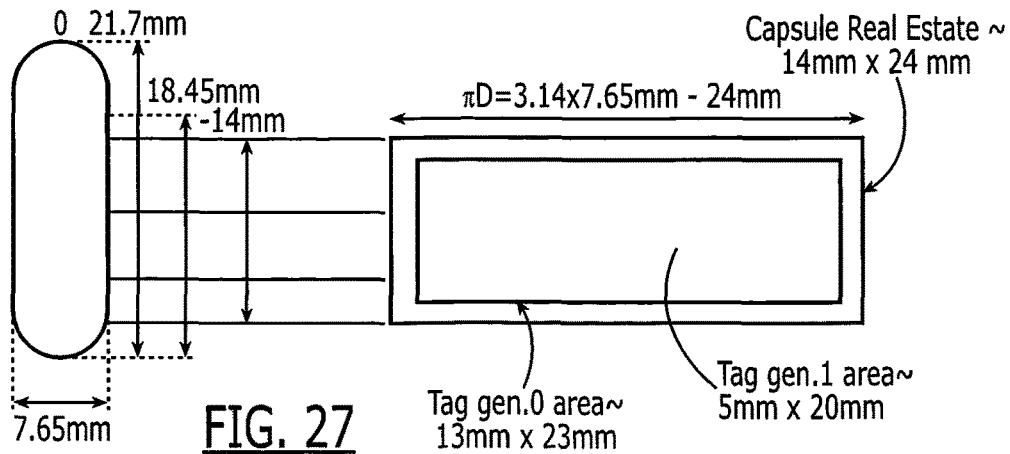
FIG. 27
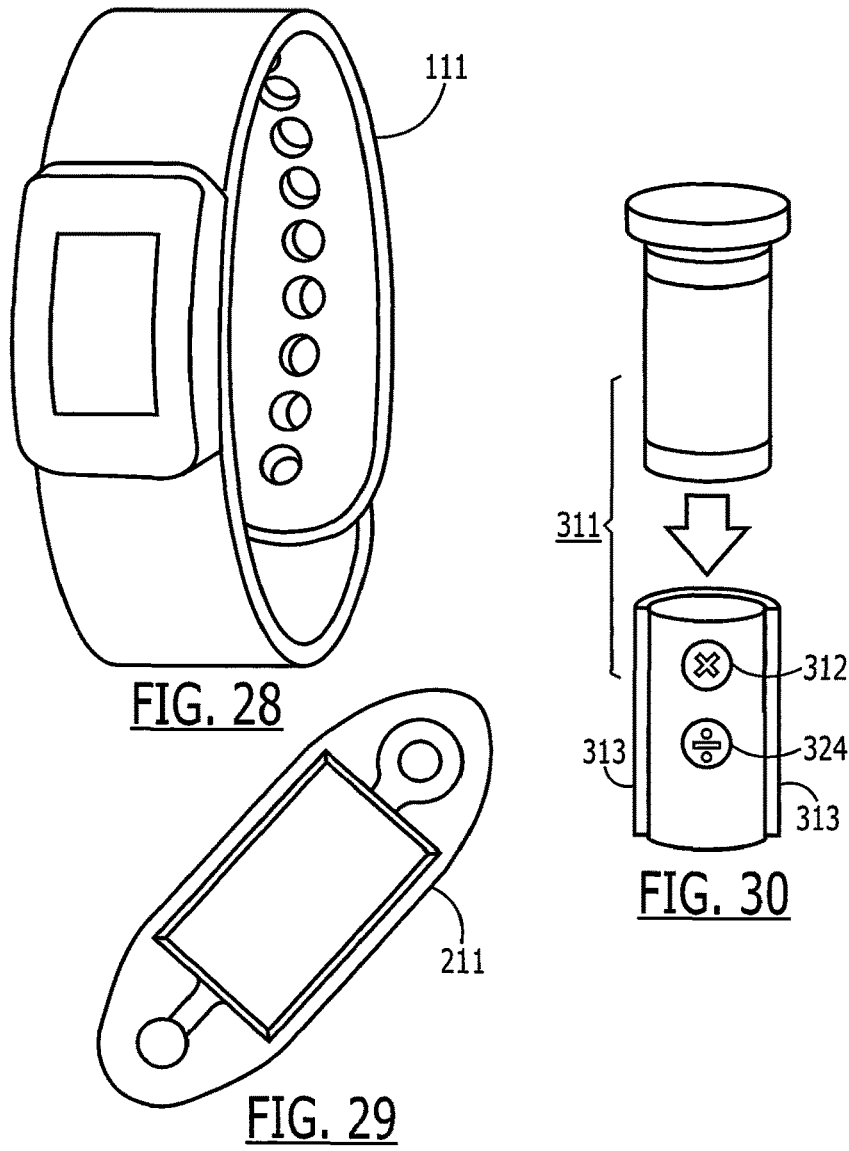
FIG. 28
FIG. 29
FIG. 30

ELECTRONIC MEDICATION COMPLIANCE MONITORING SYSTEM AND ASSOCIATED METHODS

CROSS-REFERENCE TO RELATED APPLICATIONS

This application is a continuation of U.S. application Ser. No. 14/726,899 filed Jun. 1, 2015, now U.S. Pat. No. 9,743,880 issued on Aug. 29, 2017, which is a continuation of U.S. application Ser. No. 12/881,572 filed Sep. 14, 2010, now U.S. Pat. No. 9,047,746 issued on Jun. 2, 2015, which is a continuation-in-part of application Ser. No. 11/458,815 filed Jul. 20, 2006, now U.S. Pat. No. 7,796,043 issued on Sep. 14, 2010, which claims priority to U.S. Provisional Application Ser. Nos. 60/700,963, 60/734,483 and 60/746,935, filed Jul. 20, 2005, Nov. 8, 2005 and May 10, 2006, respectively, the entire contents of which applications are herein incorporated by reference in their entirety.

FIELD OF THE INVENTION

The present invention relates to electronic systems and methods for monitoring medication compliance.

BACKGROUND OF THE INVENTION

Non-compliance of patients to drug regimens prescribed by physicians can cause a multiplicity of problems, including negative patient outcomes, higher healthcare costs and an increased risk of the spread of communicable diseases. Compliance monitoring is also critical in, for example, pharmaceutical clinical trials, geriatrics and mental health/addiction medicine. Poor medication compliance has a significant negative impact on patients, pharmaceutical manufacturers and the healthcare system in general. Non-compliant patients suffer from increased mortality, increased recurrence of chronic conditions and increased hospital and nursing home admissions. By some estimates, as much as 25% of all healthcare costs could be avoided if patients reliably took their prescribed medications.

Annual drug development spending has increased more than twelve times in inflation-adjusted dollars over the past three decades. Clinical trials consume a major portion of the development time and costs of introducing a new drug into the market. Knowing with certainty a patient's adherence significantly improves the understanding of the results from a clinical trial in terms of safety, efficacy, dose response relationship, pharmacodynamics, side effects and other results. For instance, in a beta-blocker heart attack trial the death rate was reported at 13.6% in subjects whose compliance was less than 75% compared to 5.6% in subjects whose compliance was over 75%. None of the existing methods of measuring adherence offer both a qualitative and a quantitative measure with proof-positive detection of ingestion of the medication. Accordingly, measuring medication regimen compliance continues to be a major problem. The only statistical recourse is to enroll large numbers of patients, which dramatically increases the cost of clinical drug trials that in turn increases the cost of the final marketed medication.

Compliance monitoring also provides significant benefits in market areas where patient adherence to a drug therapy protocol is vital to preventing or avoiding high-cost consequences for the patient or community. Strict regimen adherence is important for preventing emergence of drug-resistant strains of infectious diseases that can occur when proper dosing schedules are not followed. Such resistant strains result in increased transmission, morbidity and mortality and are more expensive to treat or cure, often by one or two orders of magnitude.

A traditional method of increasing compliance is direct observance, but this is obviously difficult to administer and impractical on a large scale. Other techniques include blood sampling, urine sampling, biological marker detection, self-reporting, pill counting, electronic monitoring and prescription record review. These techniques are either invasive or prone to tampering.

In vivo biotelemetry and monitoring have been used for monitoring embedded oxygen, sensing glucose levels, fetal monitoring and hormone measuring. Passive radio-frequency identification (RFID) techniques have been suggested to provide biotelemetry by including external sensors into existing commercial systems. However, RFID was not designed to operate in vivo, and the transmission of electromagnetic signals from embedded or internal sensors is hampered by attenuation and reflections from the body.

Therefore, it would be beneficial to provide an active electronic device, system and method for non-invasively monitoring drug compliance in a facile manner.

SUMMARY OF THE INVENTION

The present invention is directed to an electronic drug compliance monitoring system and associated methods that utilizes a pill having an active electronic transmission capability and external means for receiving that transmission to sense the presence of the pill in the patient's internal organs.

It is believed that the present invention has several advantages over currently known methodologies. For example, the monitor documents that the prescribed medication was actually present in the digestive system, whereas not even directly observed therapy can conclusively determine that the patient swallowed the pill. The system can be used with medication dispensers, timers, reminders, external communications, and database systems to create a complete medication compliance monitoring system. The system provides factual evidence of patient's compliance to the regimen, medication, knowledge that is critical, for example, to assessing the outcome of a clinical trial including the systematic removal of non-compliant subject data. Trials that pay subjects to participate in clinical studies can corroborate compliance. Further, the system permits remote patient monitoring whereby the monitor can be integrated into a wireless system communicating directly with a central database, reducing costs by minimizing required patient monitoring/interaction. Finally, the system is noninvasive and does not require the collection of a bodily fluid.

The features that characterize the invention, both as to organization and method of operation, together with further objects and advantages, will be better understood from the following description used in conjunction with the accompanying drawing. It is to be expressly understood that the description and drawing are for the purpose of illustration and is not intended as a definition of the limits of the invention.

BRIEF DESCRIPTION OF THE DRAWINGS

FIGS. 5A and 5B illustrate techniques used to mate an electronic tag shown in FIGS. 1 and 3 with the inside surface of a capsule (FIG. 5A) or the outer surface (FIG. 5B).

FIG. 10A is a top perspective view of an ingestible switch in accordance with the present invention utilizing a hydrogel circuit breaker.

FIG. 10B depicts the switch of FIG. 10A, with a swollen hydrogel circuit breaker after exposure to gastrointestinal fluids.

FIG. 11 is a schematic side view of a galvanic gastric sensor for utilization with the electronic tag shown in FIGS. 1 and 3.

FIG. 12A is a summary of the results of testing of several phosphate electrodes at different modes.

FIGS. 12B and 12C are coded charts depicting the results set forth in FIG. 12A for a 20K Ohm load and a 1K Ohm, respectively.

FIG. 27 sets forth representative dimensions of the capsule and tag.

FIG. 28 is a top view of a wrist band reader feature shown in FIG. 3.

FIG. 29 depicts a patch reader wearable by a patient.

FIG. 30 depicts a pill container having an on-board reader.

DETAILED DESCRIPTION OF THE PREFERRED EMBODIMENTS

A description of the preferred embodiments of the present invention will now be presented with reference to FIGS. 1-30.

Figure 1:
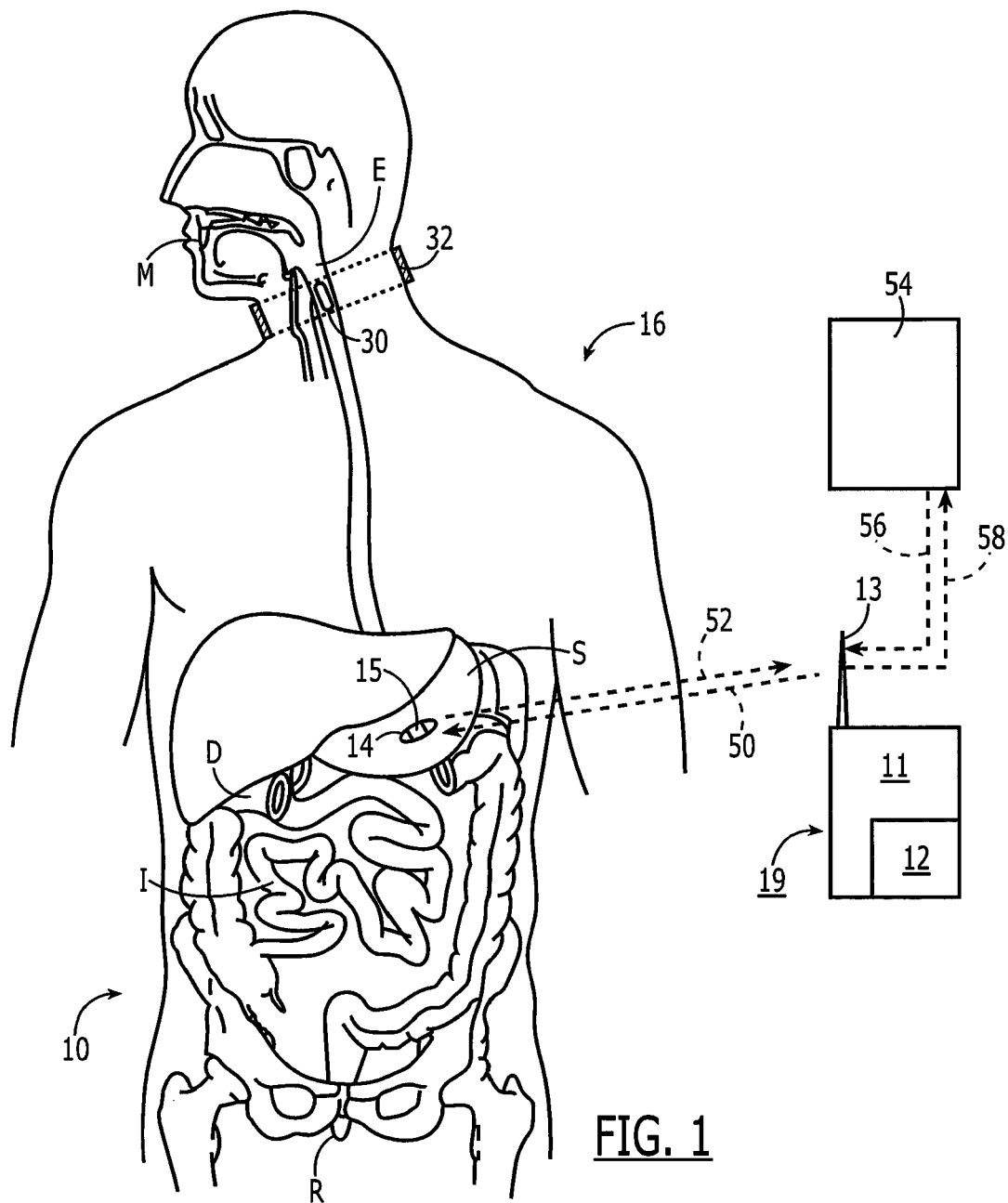
FIG. 1 is a schematic diagram of the medication compliance system of the present invention.

Noting FIG. 1, a system 10 for monitoring medication compliance in a patient 16 comprises an electronic sensor, preferably in the form of a small monitor or reader 11 that includes an RF transceiver 12 and one or more antennas 13. The antenna 13 can be external or internal to the monitor 11 and can be implemented in a variety of ways as known in the art, including an on-chip antenna or simple pads or electrical contacts that function as an antenna. The reader 11 detects the presence of an electronic pill 14 in, for example, the gastrointestinal tract of the patient 16. As shown the electronic pill 14 has a tag 15 attached to or part of the pill 14. For purposes of this disclosure, the term "pill" can include a capsule or other form of medication administration or testing. The system 10 is designed to detect the pill 14 when located in the patient's mouth M, esophagus E, stomach S, duodenum D, intestines I or rectum R.

With continued reference to FIG. 1, the system 10 includes a tag 15 fixed with the pill 14, either internally or along the outer surface, or both. After ingestion of the pill 14, the tag 15 is made electronically active and begins communication with the external reader 11. The external reader 11 in one embodiment is in a housing 19 worn by or attached with the patient 16 so as to be comfortable and easy to wear continuously to ensure it is always with the patient.

The electronic pill 14 comprises an orally ingestible and biocompatible drug-transporting device with embedded or attached electronic circuits that communicates with the external wireless reader 11. As described in greater detail below, the electronic pill 14 uses, for example, a silicon-based integrated circuit and/or other passive components such as coil antennae and capacitors. The circuit can incorporate millions of transistors, patterned through various semiconductor processing steps, to provide an enormous amount of intelligence. For instance, the electronic pill 14 can store a patient's medical history in addition to detailed information about a drug being administered, provide a unique identification number, and implement advanced communication circuits and protocols to reliably transmit data to an external wireless reader 11.

Figure 2A:
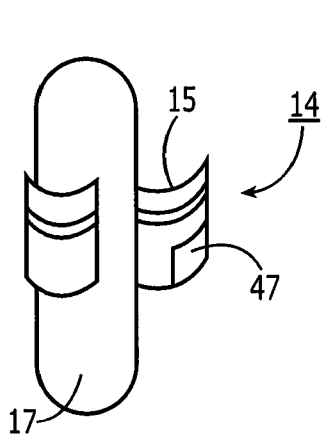
FIG. 2A is one embodiment of a capsule having a planar substrate with an antenna and electronics wrapped about a portion of the capsule.

Turning now to FIG. 2A, the electronic pill 14 preferably comprises a drug-transporting device, such as a capsule 17 that has associated therewith the electronic tag 15. Noting FIG. 1, a signal 18 received by the reader 11 from the electronic circuit 30 after ingestion of the capsule 17 is thus indicative of medication compliance. The term "drug-transporting device" is not intended as a limitation, and other compositions and devices for delivering medication are intended to be subsumed hereinto as known in the art. Alternatively, the capsule 17 may be devoid of medication to serve as a placebo during a drug trial.

Referring again to FIG. 2, the electronic components of the electronic pill 14 are capable of wireless transmission and reception over short distances (i.e., in the range of 20-30 cm). The electronic components in the circuit 20 (i.e., antenna 21, power source 22, and silicon chip 23), once hermetically sealed and packaged, is small enough to fit inside or on the outside wall of the capsule 17. This level of miniaturization is feasible owing to integration and circuit scaling trends associated with standard CMOS technologies.

With continued reference to FIG. 2A, a small chip or other electronics 47 is attached to the substrate 45 as well. This chip 47 provides a great deal of functionality including but not limited to two way communication and complex protocols, energy harvesting (mechanical, electrical, etc), sensing of conditions such as location of the tag via pH, chlorine content, etc., encryption, and identification code storage and transmission.

Figure 3:
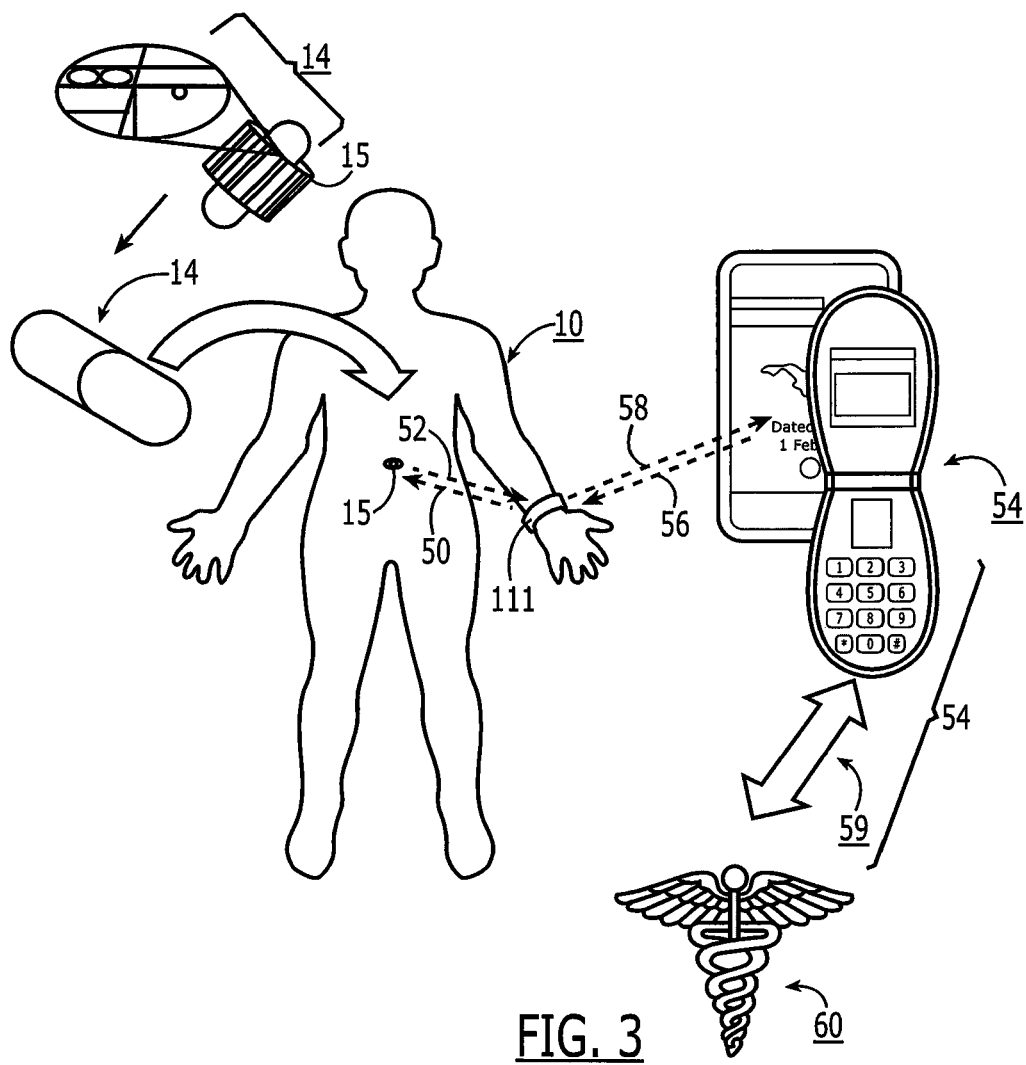
FIG. 3 is a schematic chart that illustrates the use of an electronic capsule with a wristband reader that is in communication with a cell phone, and which in turn can be used to forward information to a data collection center.

Referring now to FIG. 3, the complete system is principally composed of a Data Reader 111 and multiple tags 15 attached to medication 14. Bidirectional data 50/52 is exchanged between the reader 111 and the tag 15. The reader 111 probes the one or more tags 15 inside the body 10 and coordinates the communication to allow multiple ingested tags to communicate simultaneously, sequentially, or in other ways to permit multiple communication pathways. The tags 15 communicate their unique identification data and whether they are in the GI tract. The reader 111 then provides output data 58 to a user interface 54 such as a laptop or smartphone enabling real-time upload 59 of medication events to a remote database 60 or other location.

The data link from the reader to tag 50 is defined as the "in-link" path. Preferentially, in-link data to the tag includes synchronization, signaling, address, and tag configuration information. Preferentially, the reader 111 transmits information by way of differential metallic skin contacts. The signal passes through the body and is sensed by the tag through a differential probe network.

The data link from the tag to the reader 52 is defined as the "out-link" path. Preferentially, the out-link data to the reader includes gastrointestinal (GI) sensing, pharmaceutical, adherence, signal level, and address information. Preferentially, the out-link channel 52 is composed of a radio frequency signal traveling through both the body 10 and the free space between the body and reader antenna. A small antenna (REF) on the tag 15 radiates the out-link signal 52 which is received at the reader 111. The reader 111 is capable of receiving signals 52 from multiple tags 14 simultaneously.

All of these components work together to complete a system that can accurately detect a medication event, including the time of ingestion, the dosage, and specific identification of the medication. This information is then used to verify critical compliance with drug therapy. This data can also be used in combination with other patient data to improve adherence and treatment outcomes.

Figure 2B:
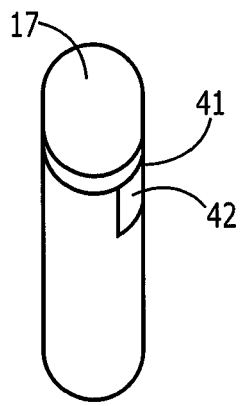
FIG. 2B illustrates a capsule having a multiple-coil antenna wrapped about its periphery.
Figure 2C:
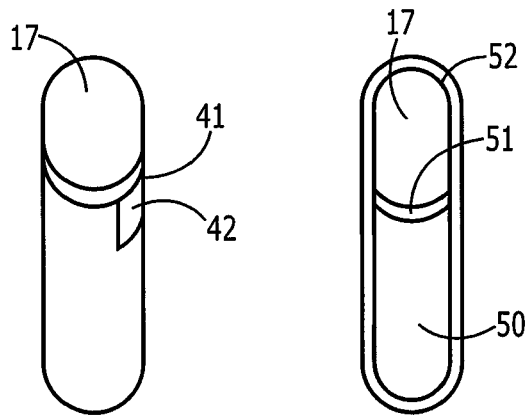
FIG. 2C illustrates a capsule having a single-coil antenna wrapped about a portion of its periphery.

In the embodiment shown in FIG. 2B, the capsule 17 has an antenna 40 printed or attached that can be detected externally. In one such embodiment, an externally induced magnetic field with a time-varying oscillatory component impinging upon a resonant tank in the pill (i.e., formed by a transponder coil antenna and a parallel capacitor located in the tag 15) causes the current circulating in the tank to increase. The peak current at the frequency of resonance can induce a small but detectable change in the reader coil impedance. Since the coils are only loosely coupled, the resonant peak detection experiment can characterize the range over which this effect can be used to detect the presence of a pill.

Marker/Tag Detail and Manufacturing

Figure 4:
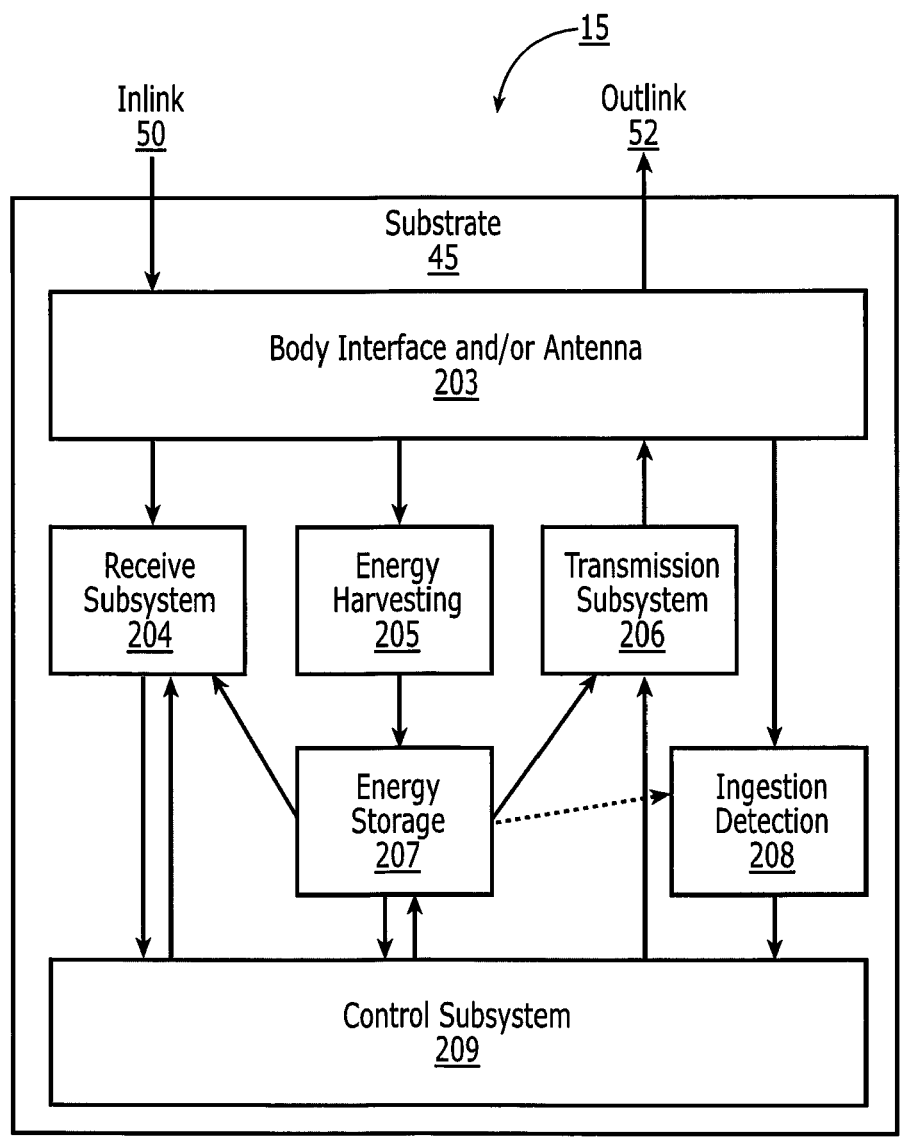
FIG. 4 is a schematic diagram illustrating the onboard electronics fitted with an electronic pill or capsule like that shown in FIGS. 1, 2A-2D and 3.

The following sections describe the detailed construction of the tag 15. Referring to FIG. 4, the tag 15 comprises a body interface and antenna 203 that allows for the in-link 50 and out-link 202 communication. The ingestion detection subsystem 208 utilizes the body interface and antenna system 203 to determine when the medication actually resides in the body 10 and in particular in the digestive tract M, E, S, D, I, R. A receive subsystem 204 implements the in-link 50 communication and interfaces between the body interface and antenna subsystem 203 and a control subsystem 209. A transmission subsystem 206 implements the out-link 52 communication and interface between the control subsystem 209 and the body interface and antenna subsystem 203. An energy harvesting subsystem 205 captures energy from either the body interface 203 or from the environment that the tag 15 resides in, for example the motion or temperature of the device. The energy harvesting subsystem 205 provides energy which is stored in an energy storage system 207 and to the tag 15 in general to operate the components and provide sufficient power for outlink 52 transmission. The control subsystem 209 coordinates and controls the differing components of the tag 15 and implements any communication protocol, sensor measurements, maintains tag memory for various identification information, and implements any other functionality required by the tag 15. The tag 15 can be attached to the medicine in a variety of ways, either by being built into the medication, build onto the medication, being printed onto the medication, or by being attached onto the outside or inside of the medication carrier (i.e. a capsule). A preferred embodiment is to build the tag 15 on a biocompatible substrate 45 that can be built in high quantities and then later attached or built into a capsule 17, for example.

Substrate (Printing and Tag)

Referring now to FIGS. 5A and 5B, in another embodiment of the tag 43 and the antenna 44 are printed on a flexible substrate 45 that is biodegradable and digestible, such as a flat sheet-like material, and includes an electronic chip 47 mounted on the substrate. This substrate 45 is then placed on or wrapped around the capsule 46. The antenna 44 is preferably printed in a way that when the material 45 is wrapped around a capsule 46, connections can be made from one end of the sheet 45 to the other, thus forming the antenna 44 as a continuous loop. Printing on both sides of the material 45 simplifies this process by using a technique similar to circuit board manufacturing with through-holes. Preferably, the substrate should have sufficient rigidity for manufacturing and attachment, be easily and safely digested, be flexible for wrapping around a pill or capsule, and withstand temperatures required for manufacturing and sterilization.

There are relatively few materials for substrates 45 and 74 that are both easily and safely digested and can also withstand temperatures required for bonding the chips 47 and 71 to the antennae 44 and 72 (up to 190° C.) or the sintering of metallic inks. In one embodiment, an enteric coating commonly used in colonic-targeted drug release, is utilized to create a flat and flexible substrate that meets these requirements and has been used in prototype tags.

Enteric coatings are commercial materials with good flexibility and proven biocompatibility. They are currently used in aspirin, acetomenophin and other drugs that upset the stomach, as they resist disintegration at low pH. Enteric coatings usually begin to disintegrate at a pH above 5.5 or higher, which is the typical pH of the duodenum and small intestine. Enteric coatings include but are not limited to polymethacrylate-polymethylmethacrylate (PMA-PMMA) copolymers and cellulose acetate phthalate (CAP), which are commercial coatings under names of "Eudragit" and "Aquacoat CPD" that are readily available as pre-mixed solutions.

Figure 6A:
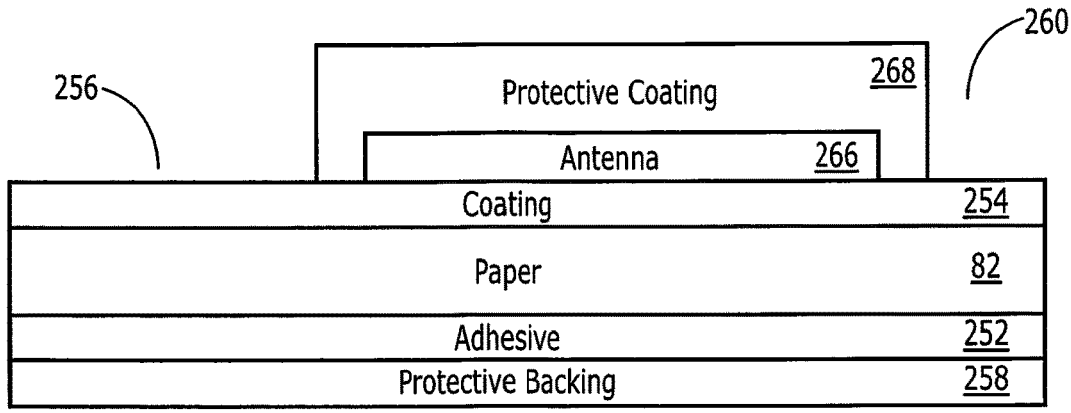
FIGS. 6A, 6B and 6C are schematic side views illustrating the layers used to fabricate an electronic tag in accordance with different embodiments of this invention.

Referring now to FIG. 6A, in another embodiment, the substrate 45 can be manufactured with a coated paper to create a biocompatible coated paper substrate system 260 to provide more advantageous properties. A paper substrate 82 coated with a coating 254 provides improved mechanical properties, increase printing strength, reduced dissolution time, and allows for alternative printing methods, while maintaining biocompatibility. Enteric coated paper provides a smooth texture 256 for the paper 82 and allows for antenna patterns 266 to be easily transferred onto it. The paper 82 also breaks up rapidly once the coating 254 dissolves. Preferentially, the paper 82 is coated on all sides, but in some implementations coating only the top of the paper is required. In addition, a biocompatible adhesive 252 is applied to the bottom of the paper when the tag 15 will be applied to the outside of the medication. When adhesive 252 is included, a protective backing 258 is used to simplify handling and attachment to the medication.

The biocompatible coated paper system 260 of FIG. 6A addresses manufacturing problems of electroplating/electro-etching on biodegradable substrates. Preferentially, biocompatible paper 82 is a mixture of biodegradable materials distributed in impregnated and/or on coated the paper in a number of ways. Paper 82 can be any substance that can be used as a flexible and strong biocompatible substrate in the dry state but weakens in the wet state. Rice papers, pulp papers, plant-based fiber papers including linen papers are all substrates that can be used with a biocompatible material coating or impregnation. The paper 82 itself is also biocompatible. The biocompatible substances 254 used for coating or impregnating the paper alter the dissolution properties, thermal properties, mechanical properties, biodegradation rates and other properties of the paper 82. The biodegradable materials included in the construction of the biodegradable substrate 260 allow for digestion of the substrates 45 and 74 and prevents untoward effects such as lodging in the stomach of the substrate or pill itself, as may occur with non-degradable and smoothly-surfaced polymeric substrates.

The substrates 45 and 74 allow for the placement of a metallic trace for antennae 266, chips 47 and 71, or other electronics via electro-plate, bonding, gluing, adhesive or printing. The antenna 266 may be covered in a protective coating 268 to prevent digestion, protect the antenna from handling, and dielectrically isolate the antenna from the enivornment. The paper 82 is superficially coated with the biodegradable substance such as polymethyl methacrylate-polymethacryalte, cellulose acetate phthalate, poly lactic acid, poly glycolic acid, various sugars, oils, waxes or proteins.

Figure 6B:
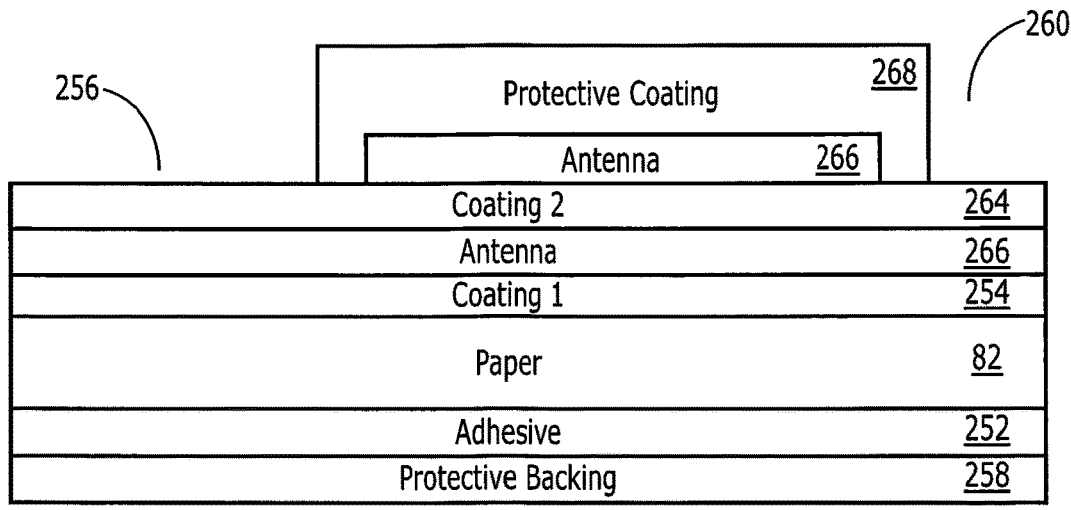
Figure 6C:
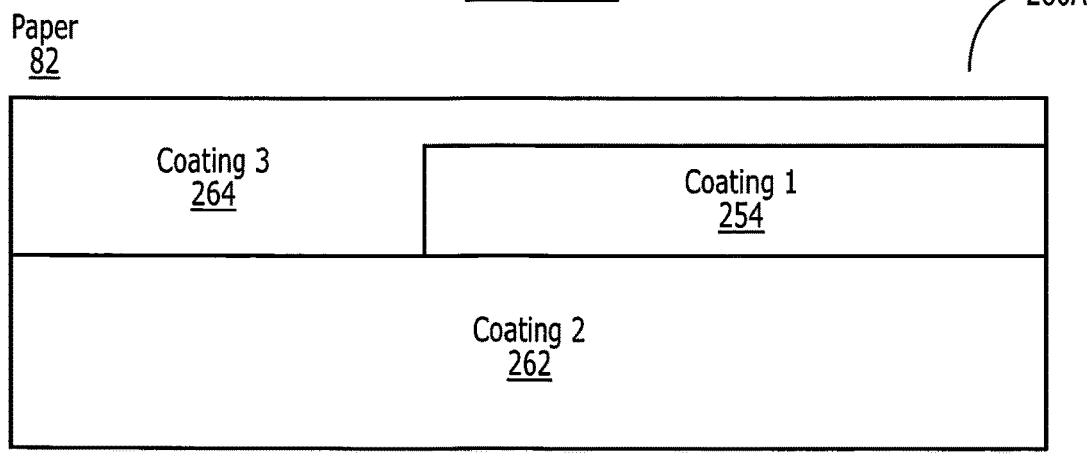

The biocompatible materials 254 added to the paper also allow for increased stability of paper materials in more extreme environments, including those of very high temperature and humidity, preventing the tag 15 from warping or deforming (and possibly fracturing the antenna 266). Referring to FIG. 6B, the substrate 45 is coated in a multi-layer or patterned method with multiple layers of coatings 254, 264 such that various portions of the tag can be exposed or broken in the body 16 at varying times or locations. At different times or locations in the body, different coatings may dissolve exposing different types or portions of the antenna 266 or sensors to the body 16. These varying conditions provide information to the system allowing for determination of ingestion time or tag 15 location. Referring to FIG. 6C, a cross-sectional side view of an alternate form of the system 260A, the coatings can be patterned such that different portions of the paper 82 are coated with different coatings. This multi-layer or multi-coated system 260A tracks the progress of the substrates as they pass through the digestive tract M, E, S, D, I, R or encounter different solutions in the body 16. In a preferred embodiment, each coating 254, 264 is an Enteric coating that is formulated to dissolve in specific areas of the human body 16. In combination with a multi-level electronic sensor and in the form of an electronic pill, the location of the medication is tracked through the human body. As each layer of the substrate 254, 264 dissolves in its pH or chemically sensitive environment, a new electronic sensor, which by way of example can be a galvanic cell is exposed. In addition to exposing different sensors or probes in different portions of the body 16, the selective dissolution of the coatings in different parts of the body 16 alters the transmission properties of the antenna 266 or system 260A in general, thus making the location of the tag 15 in the body detectable without separate sensors.

Various bodily chemicals and even organisms (and their respective chemicals) can cause the degradation of the materials used with the systems 260 and 260A. Enzymes, hormones, cells (blood cells), proteins, acids, ions, bacteria, and so forth can contribute to the degradation of the substrates or any of the substrate layers.

Furthermore, in another embodiment, the system 10 is triggered to dissolve in the patient's body 16 in the presence of both a bodily chemical and an external impulse for additional control. For example, the sensitivity of chemical breakdown is enhanced by the application of RF energy to the substrates 260, 260A (producing heat or otherwise) from an outside RF source.

The system 10 may also be loaded with various degradation control chemicals that can delay or hasten degradation rates. This is useful if the processing of substrate layers that require extra-thick amounts of a certain layer to be mechanically stable or if a layer requires another chemical in addition to the ones found in the human body 16 to begin degrading appreciably.

Antennas and Coatings

Pill or capsules 14 is typically printed with edible inks of pharmaceutical grade to uniquely identify the product and provide additional information such as company logo, brand name, and dosage information. In accordance with this invention, these edible inks are replaced with conductive and biocompatible silver inks to pattern small antennas 266 (FIG. 6A), coils 41 (FIG. 2C) or deposited conductive pattern 44 (FIGS. 5A, 5B) directly on the capsule 14, 17. Other compositions known in the art are also contemplated such as but not limited to carbon black, iron, gold, copper, zinc, and conducting polymers.

Thus, by way of printing, etching, or electroplating, miniature antennae 266 are made of silver, carbon black, copper, or other biocompatible coatings. Silver, copper, zinc and other metals are substantially biologically inert, and when ingested in small amounts, are nontoxic to humans and pass through the body without being absorbed into tissues. Furthermore, the conductivity of most of these metals is very high, making them excellent conductors. Therefore, the antenna 266 performance not only depends on physical size constraints, but also on the total usable concentration of conductive material.

Coatings. Referring again to FIGS. 6A and 6B, it is preferred to encapsulate the components of the tag with a coating 268 for multiple reasons, including but not limited to: electrical isolation from the conductive fluids of the GI-tract M, E, S, D, I, R, prevention of dissolution or exposure to the body for safety, and selective dissolution at different locations in the body 16. For example, the coating 268 prevents contact with the body, limiting exposure of the materials to the patient 16. Certain coatings can be utilized that are pH or otherwise selectively dissolved in different portions of the GI tract. In a preferred embodiment, enteric coatings that do not dissolve until they reach the intestine I or other locations, where very little digestion occurs. This allows the material to break up before excretion but not leach materials into the blood stream. It is also desirable to activate the tagging system only after the patient has ingested the pill 14. Once ingested, the pill 14 is exposed to stomach acids that eat away coatings 268 on the surface of the capsule 17, 46. Coatings 52 (or 268) may be applied or selectively applied to cover parts of the tag or capsule/pill. In one embodiment, these coatings 268 are applied selectively to cover certain portions of the tag and capsule but allow other portions of the tag and capsule to break down. This allows the tag to change shape or break down in such a way that it easily passes through the digestive tract while still protecting sensitive materials from digestion.

In another embodiment, the conductive layers of the antenna 266 on the tag 15 are made by incorporating a metal that can dissolve, such as iron filings under a temporary protective layer 268 such as polyglycolic acid or by incorporating particles that are nontoxic by virtue of being non-absorbable (e.g., silver or carbon). Degradation of the matrix releases particles that move through the digestive system of the patient 16 without absorption. Such particles are present above a percolation threshold for conductive "contact" (within 1000 Å), and reside in a degradable matrix such as polylactic/glycolic acid or starch. The degree of conductivity is adjusted by the degree of close contact and by the number of contact points (volume fraction). Particles that are not spherical can be added at lower levels to get good conduction. Hence, graphitic carbon plates can reach a percolation threshold at lower levels, and silver can be used as planar particles as well.

In a preferred embodiment, the integrated circuit 47 is encapsulated or coated in a protective coating such that it is not exposed to the body 16 and its digestive process. Packaging preferably does not interfere with the RF communication but provides enough safety for human studies. Methods of use allow access to the aqueous environment for sensors while still ensuring safety.

Energy Harvesting

Power sources for body-powered electronic pills must be biocompatible, small in size with the appropriate form factor, capable of delivering high power with good maximum discharge current characteristics and low self-discharge, and provide long calendar life. Referring to FIG. 4, many techniques exist for harvesting power 205 and storing the power 207 within the circuit 47 for use with the tag 15. For example, a simple capacitor can be used to store the energy at block 207 owing to the short duration of the active nature of these devices (less than 1 minute). The capacitor is embedded into the pill electronics and charged from block 205 by a handheld device via a magnetic field or other mechanism before being swallowed by the patient 16. The capacitor holds this charge until activated by a triggering mechanism, such as the dissolving of a specially coated switch by stomach acid.

In one embodiment of the energy harvesting block 205, the chemical energy of the stomach contents is converted into electrical energy. For instance, the chemical reaction between the stomach acid and a zinc electrode oxidizes the zinc, creating an electric current via a metal electrode making the return path. In another embodiment, the system converts mechanical motion (e.g., peristaltic and other motion common in the digestive tract) into electrical energy.

Figure 15:
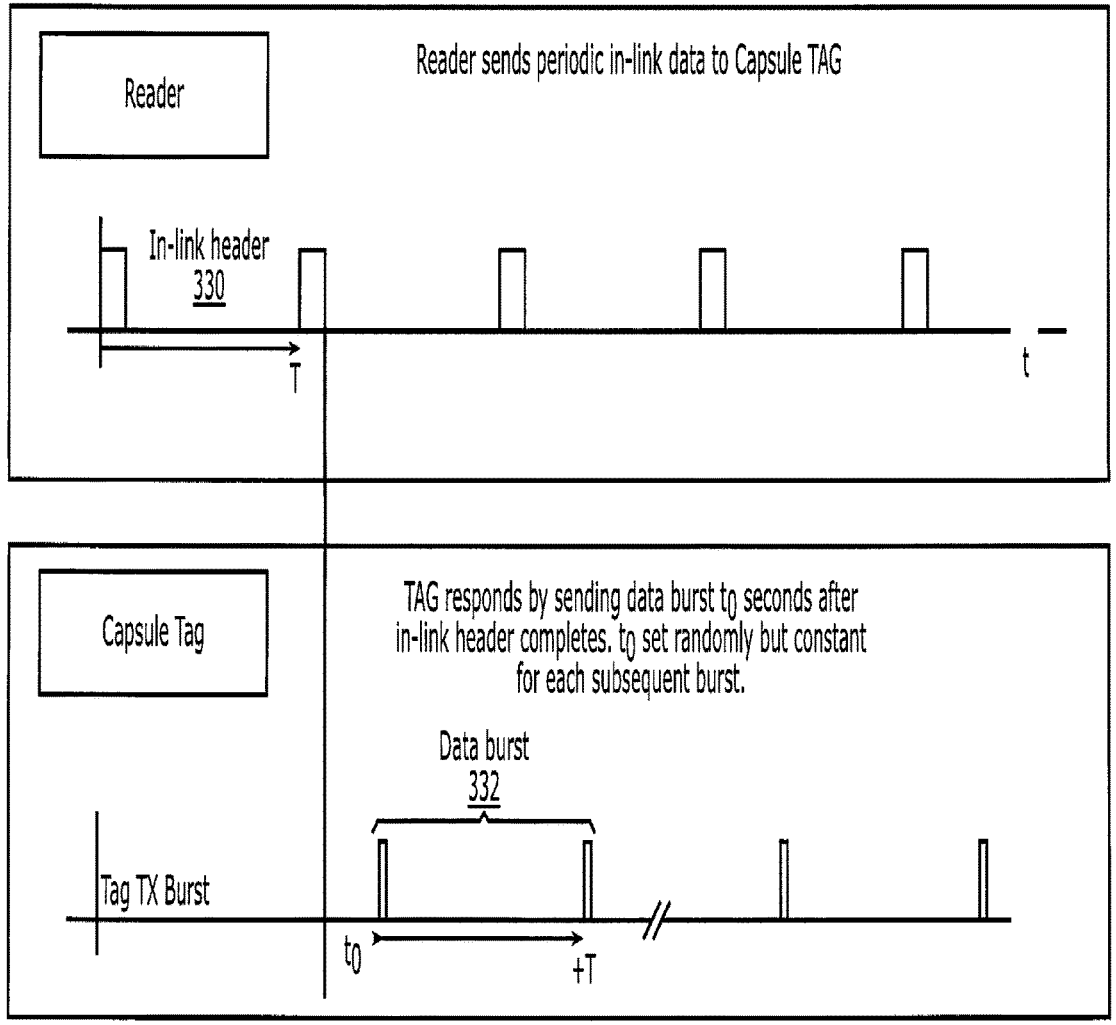
FIG. 15 is a timing chart illustrating the periodic transmissions from the reader to the tag and the data bursts from the tag to the reader.

In one embodiment, the energy harvesting system 205 harvests the energy of the inlink channel 50, stores the energy in block 207 and uses this energy to power the tag 15 and transmit data via the radiative outlink 52. Harvesting of the energy from the reader's inlink 50 is sufficient to power the tag 15 and its transmission of the outlink channel 52. In a preferred embodiment, the tag 15 harvests the energy in the inlink signals 50 until it obtains sufficient energy to transmit a signal to the external reader 11 along the outlink channel 52. As illustrated in FIG. 15, this harvesting process typically is substantially longer than the duration of the burst information sent out by the tag 15, thus allowing for amplification of the outlink channel 52 with respect to the instantaneous power harvested from the inlink channel 50. For example, if the inlink channel 50 is harvested for 100 ms and the outlink burst of information is 1 ms in duration, the outlink power transmission 52 may be 100 times larger than the instantaneous power harvested by the pill 14 from the inlink signal 50.

Ingestion Detection

An important aspect in successful detection of the ingested electronic pills is to positively identify the origin of the transmission, that is, whether the pill 14 is transmitting from inside the patient's body 16. Knowledge of transmission origin is necessary to detect a patient who might intentionally spoof the system into registering a positive compliance. Multiple methodologies can be implemented for ingestion detection with sending element 208. Noting FIG. 17, multiple techniques exist for "triggering" the system to respond only after reaching the stomach. The trigger can be activated by the dissolving of material that opens (or closes) a switch. The trigger can be based on electrical, chemical, or mechanical detection of stomach or GI tract contents (e.g., pH sensor, ISFET, temperature sensor, three electrode electrochemical cell, MEMS, microfluidics, miniaturized or nanoscale lab-on-a-chip, biomarker targeting, biosensors, optical sensor, sound transducers, bio- or chemi-luminescent sensor, etc.). When spoofing is not an issue, the trigger can be activated just before ingestion or by the reader 11. Additionally, one also simultaneously measures changes in material properties such as physical size (swelling), magnetism, polarizability/polarization, phase (solid-solid, solid-liquid, liquid-liquid, etc.), viscosity, chemical/molecular makeup, optical clarity, thermal conduction, state of charge and so forth. In one embodiment, the sensor senses changes in the outer walls of a capsule, such as temperature or conductivity before it comes in contact with the outer environment.

The ingestion detection system using the galvanic gastric sensor 284 (FIG. 11) with sensor 208 communicates with the control subsystem 209 of FIG. 4. The control subsystem 209 is then either programmed to process the data it receives to determine if the tag 15 is in the proper location, or passes the data through the transmission subsystem 206 for analysis by the external components, for example the reader 19 or 111, external device 54, or central database system or healthcare provider 60. In another embodiment, the tag 15 does not respond to queries from the reader 111 or 19 until the ingestion detection system 208 indicates that the tag 15 is in the proper location, such as the stomach S.

Additionally, the presence of specific features in the received signal from inside the body may be sufficient to determine the transmission origin. For instance, signal strength in outlink 52 coming from inside the body 16 is lower compared with that from outside the body due to attenuation from tissue, blood, and bones. It is also reasonable to expect a shift in the resonant frequency or a unique characteristic of the frequency spread or content when a signal propagates through tissue, which is absent when the transmission is outside the body 16.

Additional techniques for detecting the origin of the transmission of tag 15 include:

1. The dynamics of pill motion in the esophagus E (e.g., speed of pill travel, orientation of magnet, and path of travel) and or stomach S may provide subtle discriminating differences between the inlink signal 52 received from tag 15 inside the body 16 and a tag 15 that is outside the body. The peristaltic motion of the esophagus and the tossing and turning in the stomach may produce pill motion that affects the signals received due to the natural or purposely modified directionality of the fields generated by tag transmission. Additionally, there is a normal progression from mouth M to esophagus E to stomach S that will produce a difference in motions that must be obtained sequentially to validate the location of the pill 14.

2. Transmission of unique codes based on a variety of potential sensors attached to the tag 15. In one embodiment, body temperature and/or pH sensors are included in the ingestion detection system 208 and either processed or relayed by the control system 209 to the transmission subsystem 206. The control subsystem 209 can transmit either raw sensor back to the reader 111 or 19 for analysis of the patterns, or process the data itself and transmit back to the reader 19 (FIG. 1) or 111 (FIG. 3) an indication of its location.

3. Ensuring that the pill 14 is only active inside the patient's body 16. For instance, the pill 14 is inert when dispensed and is activated upon contact with saliva and/or other bodily agent.

4. Alternatively, the pill 14 is activated outside the body 16, prior to ingestion, and deactivated inside the body 16 after coming in contact with bodily fluid.

The activation/deactivation process can be carried out using, for example:

1. Selectively coated sensors that exhibit change in properties in the presence of specific chemical compounds.

2. Biodegradable switches based on proteins that are broken down when exposed to digestive enzymes in the stomach.

3. Unique GI fluid sensors based on the properties of the GI fluid.

Figure 7:
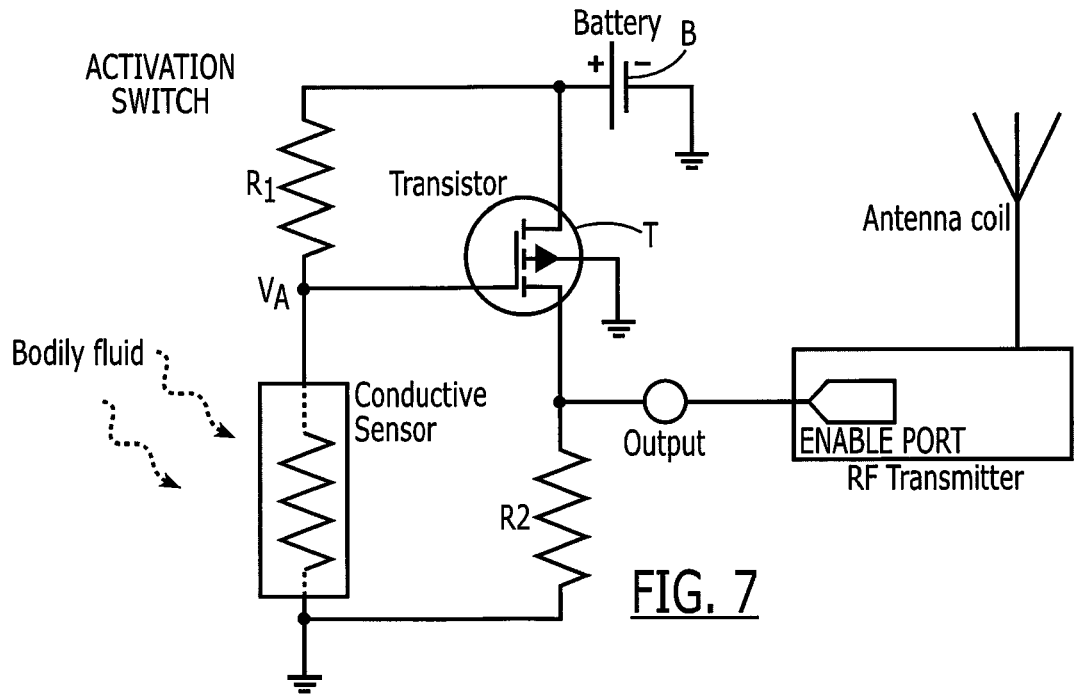
FIG. 7 is a circuit diagram for an exemplary activation switch circuit using a conductive sensor with a NMOSFET transistor.

Conductive sensors. One implementation strategy of a bio-switch is to interface the conductive sensor with a transistor (e.g., MOSFET, FET, BJT, etc.), as shown in FIG. 7. A conducting sensor in series with resistor R1 acts as a simple resistor divider and provides the necessary biasing voltage to the transistor gate. The output of the bio-switch is taken from the transistor drain and fed to the enable port of the RF transmitter (an RF transmitter is used as an example, but can be any electronic device that requires activation). A power source provides necessary power to drive the transistor and activation voltage. When the bio-switch is outside the body, the resistance of the conductive sensor is small compared to R1; thus the activation voltage (VA) will be below the gate threshold voltage. When the gate voltage is below the threshold, the transistor is turned off and the voltage at output equals zero. When the bio-switch comes in contact with a bodily fluid, select chemical molecules will bind to the conductive sensor and increase its resistance, thereby also increasing the activation voltage. When the activation voltage increases beyond the gate threshold voltage, the transistor turns on, and voltage at output equals that of the battery. A large voltage at the output in turn enables the RF transmitter and readies it for transmission.

Figure 8:
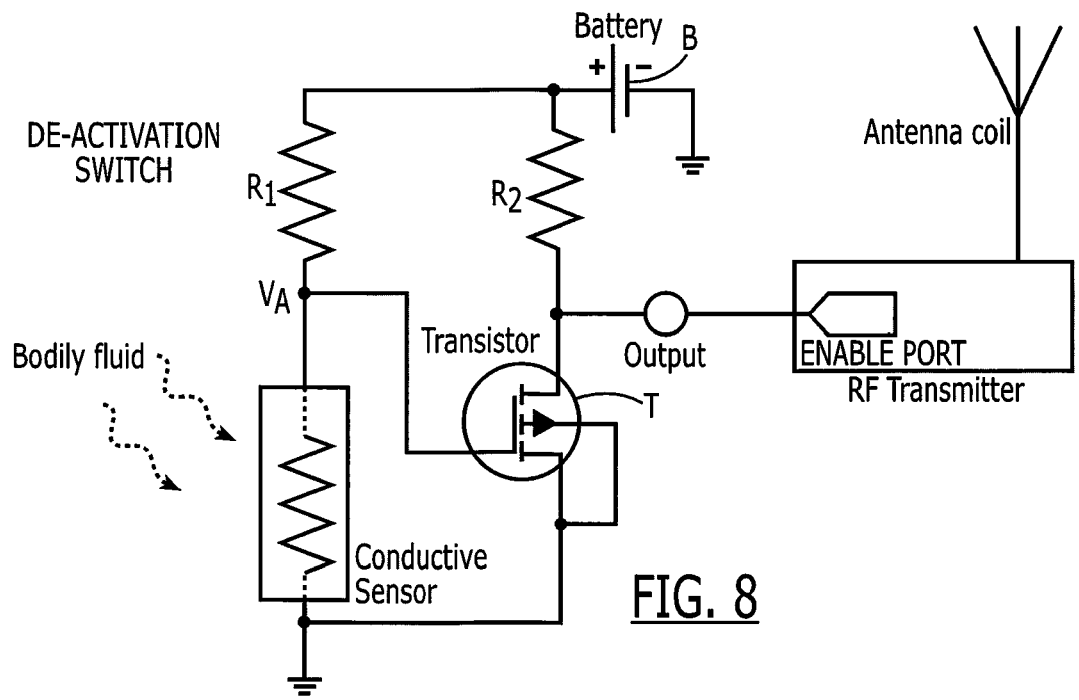
FIG. 8 is a circuit diagram for an exemplary deactivation switch circuit using a MOSFET transistor.

An alternative implementation is shown in FIG. 8, where the circuit configuration yields a deactivation circuit. When the bio-switch is outside the body, the voltage at output equals that of the battery; that is, the RF transmitter is enabled. When the conductive sensor comes in contact with a bodily fluid, the transistor is turned on and voltage at output equals zero, thereby disabling the RF transmitter.

A bio-switch implementation using a conductive sensor is not limited to the above examples. Variations in transistor type, substrate type, biasing schemes, selection of power, etc., can yield several different implementation options. An exemplary concept here is the utilization of a conductive sensor to drive a switching mechanism. In the above examples a battery was used to drive the transistor and circuitry, but instead a charged capacitor can easily replace the battery. The switch can also be used to modify the frequency of the signal transmitted or detected externally (e.g., changing the frequency response of the pill/antenna). The capacitor can be charged before a pill is dispensed or can be charged by RF induction as is done in RFID techniques. One positive aspect of using a capacitor is that over time the capacitor will discharge and the entire system will become inert, meaning the subject must take the pill within a given time frame, thereby increasing the robustness of the system to spoofing.

Figure 9:
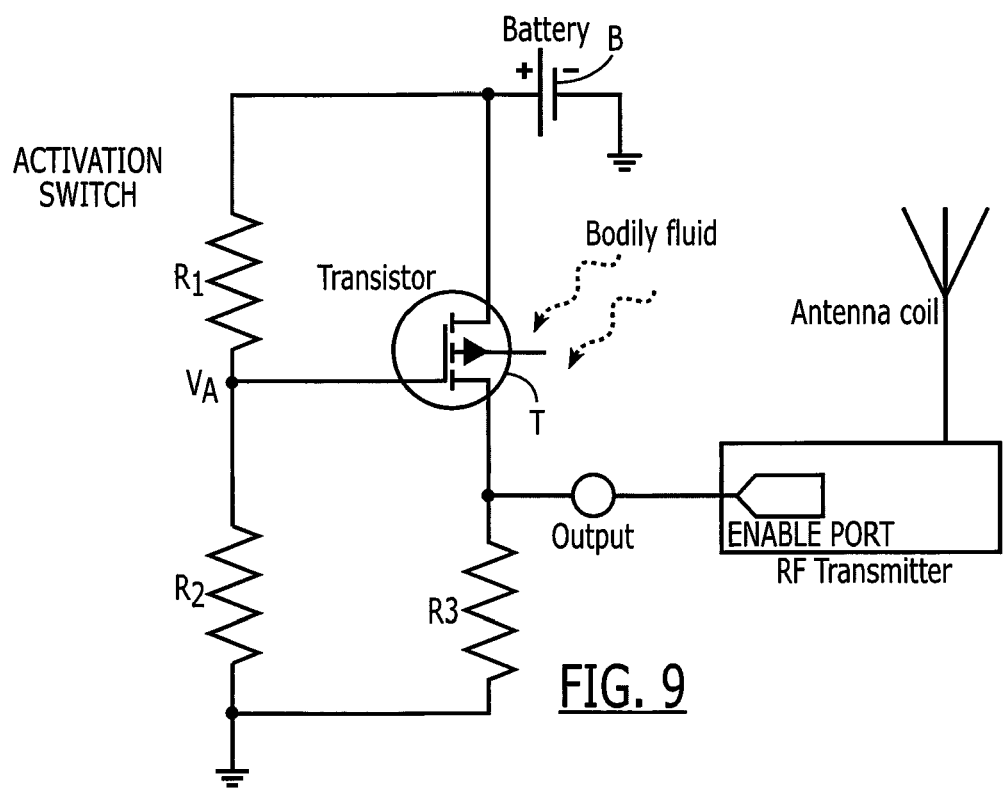
FIG. 9 is a circuit diagram for an exemplary MOSFET sensor-based bio-switch.

MOSFET sensor. Another implementation of the bio-switch is to use a MOSFET e-nose sensor instead of a conductive sensor. A bio-switch with a MOSFET e-nose sensor can be implemented with much simpler supporting circuitry since the transistor does both sensing and switching. An example is shown in FIG. 9. The resistor divider of R1 and R2 provides a fixed activation voltage to the transistor gate. When the bio-switch is outside the body, the activation voltage is just below the gate threshold voltage; therefore, the transistor is off. When the MOSFET sensor comes in contact with a body fluid, a catalytic reaction takes place at the transistor gate and changes the channel conductivity; i.e., the gate threshold voltage is lowered so that the activation voltage is now above the threshold voltage. Therefore, the transistor turns on, and the voltage at output equals that of the battery. Again, this illustration is just one possible implementation scheme, and variations can be constructed with different types of substrate (e.g., n-type and p-type) and supporting circuitry.

An additional embodiment utilizes biodegradable switches that undergo significant changes in conductivity when exposed to the digestive enzymes of the stomach. One can mix a conductive substance (e.g., carbon) with a non-conductive substance (e.g., protein). A conductive substance doped with a non-conductive substance will tend to have lower conductivity (high resistance) than a pure or even semi-doped material. When the doped material comes in contact with digestive enzymes, the non-conducting material is broken down or dissolved by the enzymes, leaving behind just the conductive material. One possible switch implementation can be based on a composition of carbon and albumin. The albumin protein is broken down by pepsin, an enzyme that is naturally present in the stomach. When the switch composition is devoid of albumin, the conductivity of the switch increases and bridges a gap in the circuit to complete the circuit. A number of possibilities exist in selecting a conducting material and a protein. Furthermore, it is also possible to incorporate multiple non-conducting materials to yield switches that are extremely selective to activation.

In the embodiment shown in FIG. 4, the in-link 50 signal is used for energy harvesting 205 and the in-link signal 50 is sufficiently low in frequency such that most of the energy is transferred galvanically through the body of the patient 11, the tag 15 is only easily powered when the tag 15 is in contact with the body of the patient 11 since the in-link signal is significantly attenuated in the air. As such, the tag 15 will not respond to queries from the reader 11 until such time as the pill is being touched or ingested by the patient 11. This provides a level of spoofing prevention with virtually no additional complexity added to the system.

Noting FIGS. 10A and 10B, in order to ensure that the pill is ingested, the antenna system can be disabled by electrically "shorting" the antenna through the use of an ingestible switch 90 that contains a circuit breaker 92 that becomes modified in the presence of gastric juice. An embodiment of this concept includes a method of breaking a circuit via the swelling of the breaker material in the presence of stomach fluid. The switch 90 comprises a thin layer of hydrogel 92 partially coated with a conductive trace 94 such as metal flake or micro-thin metal foil. When the hydrogel is exposed to low pH liquid, it swells to about sixteen times its normal size and breaks the conductive trace 94. This mixture is then coated with an albumin-based layer that will prevent exposure of the hydrogel to fluids until the albumin is selectively broken down in the GI tract by either pepsin or typsin. The preferred mechanism for deactivating the system using an ingestible switch 90 is to electrically connect the two pads of an antenna 13, creating an electrical "short". The lower the resistance, the more power is diverted from the signaling antenna. By way of example, a five ohm resistance is sufficient to reduce the input power from the antenna by 95+%. A resistance of 10K ohms will reduce the input power to the signaling chip by only 10% or less. In the case where the in-link 50 is separate from the out-link 52, either antenna can be shorted by this technique, essentially crippling the tag 15. The preferred embodiment is to short the in-link antenna in a system that utilizes the in-link to power the system.

Sensor such as pH sensors and other chemical sensors are fairly complex devices. Noting FIG. 11, to avoid a requirement to embed such a complex device into the tag 15 or integrated circuit 20, the preferred embodiment of a gastric sensor 208 utilizes a galvanic couple 208 that is placed in various bodily fluids (stomach fluid, esophageal fluid, GI fluid, etc.) to create a measurable change in electrical properties such as current, voltage, and/or resistance and allow digestible electronics to evaluate the location of a tag 15 in the human body 16. In one embodiment, the sensor 208 senses changes in the out walls of a pill 14, such as temperature or conductivity before it comes in contact with the outer environment. In the preferred embodiment, the galvanic couple can provide discrimination of location as well as providing electrical power to the system. The ingestion detection system 208 on the tag 15 works either outside or inside a pill 14. Inside the pill, the detection system 208 operates when the GI fluids permeate the pill or dissolve any external layers. The tag 15 begins generating power and voltage as soon as it is wetted by ingestion and allows the tag 15 to begin communicating with the reader 111. As the tag moves through the GI tract M, E, S, D, I, R, the sensor or voltage information is communicated or processed by the control logic 209 such that location information can be determined by the reader 111 or other external system. FIG. 11 shows the GI sensor/energy cell connected to control logic 208. The GI sensor requires two electrodes for operation and one or both of these electrodes may also function as antennas. In the preferred embodiment, one of the electrodes for the GI sensor comprises a small strip of metallic zinc while the second electrode consists of a specially coated silver electrode that is shared with the inlink antenna.

In one embodiment, the galvanic couple 284 is constructed of two differing metals 280, 282 or compounds that, when placed in a bath of any number of solutions, produces an electric voltage and subsequent current and is measured by the control system 208. Metals used for a galvanic gastric sensor 284 are transformed by a number of chemical reactions to produce a new chemical compound. The new compound changes the differential voltage. Upon immersion in a target fluid, the compound transforms into a different compound and accompanying the transformation is a change in voltage. Other changes in the galvanic cell materials can be phase transitions, state transitions, amount of the chemical compound (causing a natural change in differential voltage based on the degree of material available to sustain such a voltage), and other materials transitions that cause a change in the electrical output of the galvanic cell. In the preferred embodiment, the GI sensor creates varying degrees of current or voltage depending on the nature of the fluids in which it is immersed. Thus, the GI sensor not only gives true/false data about the environment, but may also senses the chemical/electrical/thermal/etc. makeup of the environment and give a signal corresponding to the state.

The metals or compounds are connected to a measurement means in the control logic 208 (FIG. 11) and can be a voltmeter, potentiostat/galvanostat, electronic switch or other means to measure or gauge the voltage and report if and/or when the target electronic reading is reached in the target solution. If the sensor 284 is not in the target solution, the voltage will not change appreciably as no chemical transformation will proceed. Thus, the voltages or an indicator of location can be transmitted via the tag 15 to the reader 11 or 111 to confirm the location of the pill 14. Such chemicals transformations include silver phosphate and other silver compounds, including silver chloride, silver sulfate, silver carbonate, or even silver metal itself. Transformation can occur on the anode or cathode of the galvanic cell. In the preferred embodiment of FIG. 11, a silver phosphate electrode 280 is attached to a zinc electrode 282, and the silver phosphate transforms to silver chloride and silver metal while the zinc oxidizes to zinc metal or forms a zinc compound with anions in solution. Accompanying the silver materials transformation is a voltage differential (from high-to-low or low-to-high state). The voltage/current differential is affected by the selection of the two metals or compounds (or mix thereof), whereby a silver phosphate-zinc system differs in output voltage/current from that of a silver-phosphate-copper or silver sulfate-zinc system. Furthermore, a dissolvable or protective coating 281, 283 may be applied to the electrodes 280, 282 such that the electrodes are not exposed to the fluid until a certain external condition exists, such as when the tag 15 is exposed to the high chlorine content of the stomach. Coatings on each electrode 281, 283 can be the same or different, providing flexibility in the voltages and currents produced in different transit times and locations in the body 16.

FIG. 12 is a chart describing the voltages measured from the silver phosphate electrode 280 of FIG. 11 formed by applying 9V to a silver chloride electrode in KH2PO4 solution with a silver electrode return path 282. The silver phosphate electrode 280 was tested at loads of 20 kOhm and 1 kOhm. The charts in FIGS. 12A, 12B and 12C show the time course of voltages of the electrodes with differing amounts of phosphate (exposure time to the KH2PO4 solution), differing loads, and differing solutions. The gastric sensor 284 has a substantially different voltage in HC1, the primary component of stomach fluid, versus sulfuric acid solution.

In alternate embodiments, the tag 15 is modified to include sensors to provide the ability to access the tag's internal memory. For instance, the tag 15 can have a pH monitor, temperature probe, or other sensors 42 (FIG. 2C) to verify compliance. In addition, it may be beneficial to use a system that can also provide a readout of the signal strength. This signal strength is beneficial for optimizing the communication protocol dynamically as well as providing potentially discriminating information relating to the location of the tag 15.

Biometrics

In addition to determining when the pill 14 is ingested and where it resides, it is important to detect that the pill is ingested by the appropriate person. As such, a variety of biometrics are utilized to detect that the reader 111 and/or pill 14 are located on or in the correct person 16.

In one embodiment, an electronic pill monitors physiologic signals inside the body 16 that are typically difficult to mimic outside the body. For example, the patient's electrocardiogram (ECG) is detected and measured by the electrical contacts or antenna of the tag 15. The tag 15 either processes the signal or passes the signal via the outlink 52 to the reader 11 for further processing. Detecting the presence of a valid ECG signal indicates that the tag 15 is inside the body 11. Detection of a periodic pulse between 30 and 120 BPM is sufficient to detect that the tag 15 is inside the body. Furthermore, a wide variety of parameters can be extracted from the physiologic signals detectable inside the body 16. In a preferred embodiment, the processing system (either in the tag 15, reader 11, or elsewhere downstream) detects parameters of the electrical characteristics of signals received inside the body 16 including but not limited to: periodicity, amplitude, signal shape (including peak geometry, relative height), and signal to noise ratio. In addition, the signal detected inside the body can be transmitted to the reader 11 and verified against a preloaded signature of the ECG or other physiologic signal recorded earlier, for example, during the initial administration of the system 10. Additionally, the reader 11 can record the same signal outside the body 16 and ensure that the tag 15 is in the same person 11 that is wearing the reader and also checked against the stored signature. These features of the ECG and other physiologic signals measured at the tag 15 or reader 11 are also capable of biometric identification.

These physiologic features and their dynamic features (changes in the signals over time) are useful to identify the patient 16, ensure ingestion, or determine the location of the tag 15 in the digestive tract M, E, S, D, I, R. The dynamic features include but are not limited to heart rate variability, changes in signal strength as the tag moves through the body 16 and muscle activity in different parts of the body. For example, the ECG will be quite strong as the pill passes the heart in the esophagus E and then gradually get weaker as it moves farther from the heart in the GI tract S, D, I, R.

In an embodiment, the external reader 11 is used to monitor and assess a given patient's 16 ECG output (periodicity, peak geometry). This information is used for a first calibration step and recorded as the baseline ECG output. The later measurement of the ECG by the reader 11 validates that the same person is using the reader. Additional, the measurement by the tag 15 can be checked against this calibration to ensure that the proper person is taking the medication. In this case, if either the medication or the external reader is switched to a different person 16, the results can be checked against the calibration data. Calibration can take place in the presence of proper supervising personnel, including doctors, nurses, etc., and the calibration can be locked to those who either have calibration codes or calibration devices.

These biometric capabilities can also be used to help guard against improper medication (type or dose) being taken. Each tag 15 can be programmed to be taken by a specific patient. The patient specificity will be recorded by certain physiologic signals that can identify individual patients, such as parameters of the ECG. The reader 11 or interface 54 can first be programmed to register the kind and frequency of medication to be taken for a given patient ECG. The reader 11 or interface 54 then alerts the patient or proper personnel if the medication taken was given to the wrong person (pill ECG does not match reader ECG) or if the medication was taken at improper time intervals (over-or under-medication).

Control Logic/Ic Design

Maximizing power efficiency is of utmost importance to maximize the reading distance between the reader 11 and the tag 15 as well as power output and detectability. Advanced low-voltage and low-power circuit design topologies and a suitable process technology are required to achieve operation with small input power levels from radiated electromagnetic fields.

Figure 13:
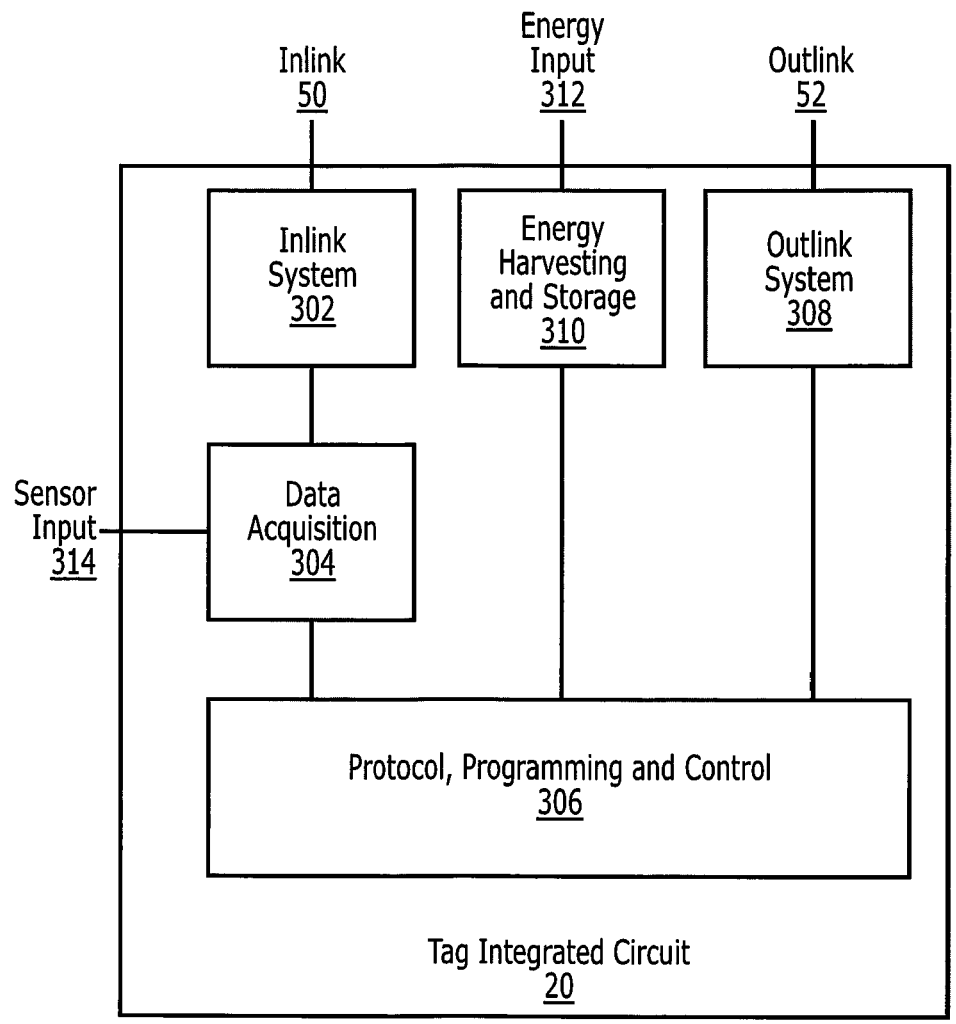
FIG. 13 is a block diagram illustrating the electronics associated with the tag integrated circuit.

Referring to FIG. 13, the preferred embodiment of the integrated circuit 20 for the tag 15 includes: protocol logic 306 having a random bit generator XXX for robust two-way communication and control, data acquisition subsystem 304 and sensor 314 to determine the strength of the in-link signal 50, inlink subsystem 302, outlink subsystem 308, and energy harvesting and storage system 310. The IC 20 is designed with fallback operating modes, including a chirp mode and a beacon mode. In the chirp mode, the protocol is suspended and the IC 20 transmits data whenever it has sufficient power from the energy harvesting and storage system 310. In beacon mode, the IC 20 transmits a periodic burst pattern with no data (bypassing all digital logic). In one embodiment, the energy harvesting and storage system 310 extracts power from induced currents generated from the external reader 11 via the inlink subsystem 302 or directly via the inlink antennas 50. In a second embodiment, a galvanic cell, GI sensor, thermocouple, or other method of generating power from the digestive tract M, E, S, D, I, R or motion through it provides primary or supplemental power via the energy harvesting subsystem 310 to enable the IC 20. The outlink subsystem 308 drives the outlink signal 52 under control of the protocol logic and control subsystem 306. The protocol and control system 306 contains all the logic to control the IC, the communications protocol, the data acquisition, synchronization, and data storage and output, including the preprogrammed information about the medication, patient, study and other information. Minimizing the power usage of all these subsystems and in particular the outlink subsystem 308 is of utmost importance.

Preferably, the IC 20 is fabricated using industry standard CMOS manufacturing processes in class 10 or better clean rooms. The physical dimensions of the IC 20 are expected to be very small, less than 1 mm×1 mm×0.1 mm. When affixed to the tag 15, the IC 20 is encapsulated in biocompatible epoxy to cover any hard edges and to prevent interaction between the IC 20 and the patient's body 16. The preferred IC 20 is a custom designed microchip that stores the medication information, reads the GI sensor, and implements the signaling and communications protocol. The IC is designed to operate with extremely low power and to provide reliable deep in vivo communications.

In addition to integrated circuit implementations for the various logic and systems of the tag 15, another embodiment includes printed electronic circuits created with various inks including metallic, dielectric, and organic materials. The creation of complex printed electronics requires the creation of multilayer electronic devices such as transistors and capacitors, silver conductive ink and dielectric materials are typically loaded into separate ink cartridges. For example, In the case of capacitors, fabrication can be achieved by first printing a single line of nanoparticles onto a substrate that is heated until the inks are metalized. Next, a dielectric of polymer is printed directly over the line. Finally, a second conductive line is printed perpendicular to the original conductive line. In this way, the overlapping cross-section of the two conductive lines—with a dielectric between them— creates a capacitor whose capacitance is defined by the overlap area and the dielectric material and thickness Thus, if an antenna is printed simultaneously and attached to each conductive line, a simple 3-step inking procedure is enough to begin creating simple inductor-capacitor antennas that can resonate at a tuned frequency.

Many generally recognized as safe (GRAS) materials are available for use as dielectrics, for example polytetrafluoroethylene (PTFE), polyimide (from precursors) and PVP. In the preferred embodiment, enteric coatings are used as a dielectric material.

Communication Links and Protocol

Transponder Antenna Size and Efficiency. The radiation efficiency of a typical loop antenna increases with loop area and is inversely proportional to the excitation signal wavelength. Since the loop area is limited, it is desirable to operate at higher frequencies to improve the antenna efficiency. In typical RF applications, operating at higher frequencies can improve the aperture efficiencies of small antennae to maximize the received power. However, in biological systems, the operating frequency is a tradeoff between increased path loss in tissue and antenna efficiency. Indeed, RF signal attenuation behavior of the inlink 50 and outlink 52 in bodily fluids and body tissue to and from an ingested tag 15 is complex and difficult to model.

The tag 15 may be coded with a variety of information including but not limited to data about medication, the patient 16, the reader 11, or the drug trial the patient is participating in. Additionally, the tag 15 can have a unique ID that is utilized with a database of other information tagged to each tag ID to obtain similar information without storing it on the tag 15. Upon detecting the tag 15, any of the readers 11, 111, 211 or 311 can store a time-stamped reading of a medication event. If the tag 15 is not detected, failed compliance can be signaled, for example, to the patient 16 and/or to a second party such as a health care provider or other agency 54 via input and output signals 56, 58.

It is preferred that the communication between each reader 11, 111, 211 or 311 and the tag 15 provides two way communication, with the communication from the reader 11 to the tag 15 being preferably through a conductive in-link channel 50 and the communication from the tag 15 to the reader being preferably through a radiative out-link channel 52. The in-link channel 50 is preferentially in the range of 1-20 MHz; this frequency range produces efficient data transfer from outside the body to deep inside the body 16 and can travel through the body galvanically, requiring very small antennas or pads only to receive the signal. Because the inlink transmissions 50 travel galvanically, the signaling attenuates very rapidly outside the body 16 thus providing for increased privacy for the inlink channel 50. Skin surface contacts with the reader, as readers 111, 211 and 311, maximizes the efficiency of the in-link transmission 50 from the reader. The in-link channel 50 communicates a variety of information to the tag 15, including but not limited to querying for the presence of the tag 15, turning the tag's transmitter on or off, collision avoidance, and various other protocol-based communications. The inlink channel 50 also provides synchronization signals between the reader and tag 15. Synchronization between the reader 11 and tag 15 are particularly important when the outlink signal 52 is very small (as is expected when coming from inside the body) and/or when the outlink signal is transmitted in very short bursts for better energy efficiency.

In an embodiment, the tag 15 is powered using the RF energy received by its coil or antenna or in another embodiment where power is generated by energy harvesting means. As described previously, this power can be stored temporarily and then used to transmit a pulse or signal to the reader 11. Storing the energy internally in the tag 15 helps alleviate two distinct problems. First, it allows for the storage and amplification of the instantaneous power received from the inlink 50 or energy input 312 to create higher powered but shorter bursts of outlink transmissions 52. Second, when transmitting into the body 16, the external powering signal (inlink 50) creates significant noise that may make detection of the outlink signal 52 from the tag 15 very difficult.

One method to create more detectable signals for outlink 52 is to utilize different frequencies for power transmission and data signaling. This allows the external receiver 12 of the reader 11 to be frequency-isolated from its transmitter. A frequency selective filter may then remove the noise from the transmitter to allow for high quality reception of the data signal. Lower frequency signals typically have lower losses in the human body. As such, the power transmission signal 50 may necessarily be lower in frequency than the data transmission signal 52 which can be much lower in power.

Another method involves the use of dual antennas on one or both of the tag 15 and receiver 12; that is one antenna or set of probes/contacts for the transmission/reception of the in-link or power transmission, the other for transmission/reception of the data signal.

As discussed in greater detail below with reference to FIGS. 15-18, another method involves the time multiplexing of the signals such that the power transmission ceases during predefined time periods to allow tag 15 to start transmitting data. The circuitry of tag 15 can be designed to utilize this cessation of power transmission as a marker to determine when to start transmitting data. Additionally, that circuitry may store the power during the "power cycle" for a period of time typically longer than the transmission cycle to provide a power multiplication to improve the signal strength of the data transmission.

It is preferred that the communications to and from the tag 15 and to and from the readers 11, 111, . . . are protected, encrypted, encoded, or made secure in a way to prevent interpretation by other devices and have software and/or hardware required to protect the data and support privacy or data security requirements of the communication system.

Although the technology described above focuses on RF technology, many other technologies are possible. The passive devices that are detected via an external sensor can include many standard imaging technologies such as X-ray, ultra-wide-bandwidth (UWB) imaging, ultrasound, or MRI devices. Each can have a transmitter that transmits energy into the body and detects reflections or distortions in the magnetic field caused by the presence of the pill (or pill contents or coating).

Many of the tag 15 embodiments support IDs and other stored data that can be transmitted back to the reader 11 via the outlink channel 52. IDs and other data can be transmitted via pulsatile signals (information in the pulse duration, pulse spacing, pulse frequency, etc.) or via digital encoding. To increase signal-to-noise ratio, it is preferable to have a transmit/receive event wherein the tag 15 responds to a request from the reader 11 with a predetermined signal. This signal is repeated and then synchronously averaged over multiple transmit/receive events to produce a better signal-to-noise ratio. Synchronization of the transmissions from and to the reader 11 and tag 15 also improves the ability of the reader 11 to detect faint signals 52 from the tag 15 in the body 16.

Figure 14:
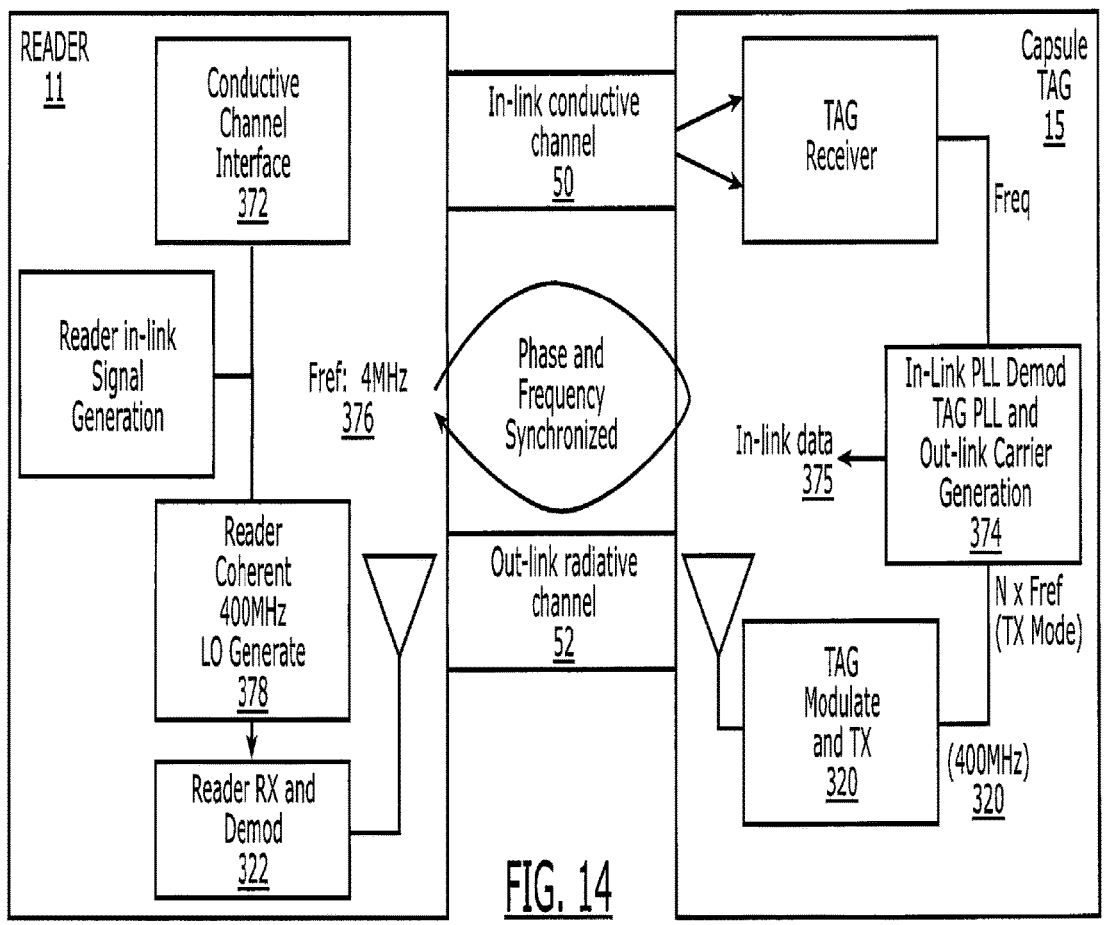
FIG. 14 is a block diagram illustrating the overall inlink and outlink communications between the electronic tag taken internally by a patient, and the external reader utilized to communicate with the tag.

An embodiment of an efficient communication and protocol approach is demonstrated in FIG. 14. The approach is based on a unique communication path between the tag 15 and the associated reader 11. The reader 11 transmits data to the tag 15 by way of the conductive or galvanic in-link 50 communication channel. The tag 15 transmits data to the reader 11 through the out-link radiative channel 52. An electromagnetic transmitter block 320 provides the interface to the radiative channel 52 at the tag 15 and a corresponding reader RX 322 extracts the signal at the reader 11. A tag 15 for a patient 16 is linked directly to the patient reader 11 similar to a key and lock. Only data with the proper key or data word are recognized by the reader 11 as valid patient data. As an extra measure of protection, the out-link TX carrier 320 is phase locked to the reader in-link signal 50 to provide means for synchronization of data. Phase lock also allows coherent detection of the tag data at the reader 11, thereby enabling use of phase modulation and reduced error rates. Since the in-link signal 50 is propagated by direct body contact (in-link conductive channel), only the reader 11 attached to the patient's body 16 can properly demodulate the return tag outlink 52 data. This feature makes external eavesdropping of the data very difficult. Hence, this approach enhances security of the data. As will be appreciated, this communication protocol also allows several tags to be consumed and data read without the need for individual tag identification bits, thus reducing significantly the amount of data that needs to be stored.

The protocol is composed of the communication link timing and the associated in-link 50 and out-link 52 data fields. FIG. 15 depicts the relative communication link timing of the data for the in-link 50 and out-link 52. The process begins with the reader 11 sending an FM modulated signal, or "in-link header" 330 to the tag 15 with information necessary for proper tag operation. The header is sent periodically every T seconds. On ingestion, a random bit generator in the circuit 20 for the tag 15 begins operation. On completion of the in-link header field 330, the value of the random bit generator is latched. This latched value is used to set the time, $t_0$ at which the tag 15 responds to the reader 11 by sending a data burst 332. The data burst 332 contains a subset of the data stored on the tag 15 to be sent to the reader 11. Several bursts 332 in sequence make up the full data transmission through out-link 52. The latched random generator value becomes the pill ID or address for this specific tag. Since the ID is random, each tag swallowed will have a unique ID. As will be appreciated by those skilled in the art, the algorithm may be as simple or complex as necessary to assure no two tags randomly end up with the same address. Each tag swallowed will send a pulse 332 delayed in time from the end of the header 330 proportional to the value of the random address. In this fashion, no two tags 15 can transmit at the same time, thus preventing interference but also allowing multiple ingestion of tags. Also, since the tag address is set randomly, there is less need for special tag identification bits to be stored on each tag, thus reducing significantly the number of bits of memory required on the tag 15. This reduces cost and complexity of the tag 15 significantly.

Figure 16:
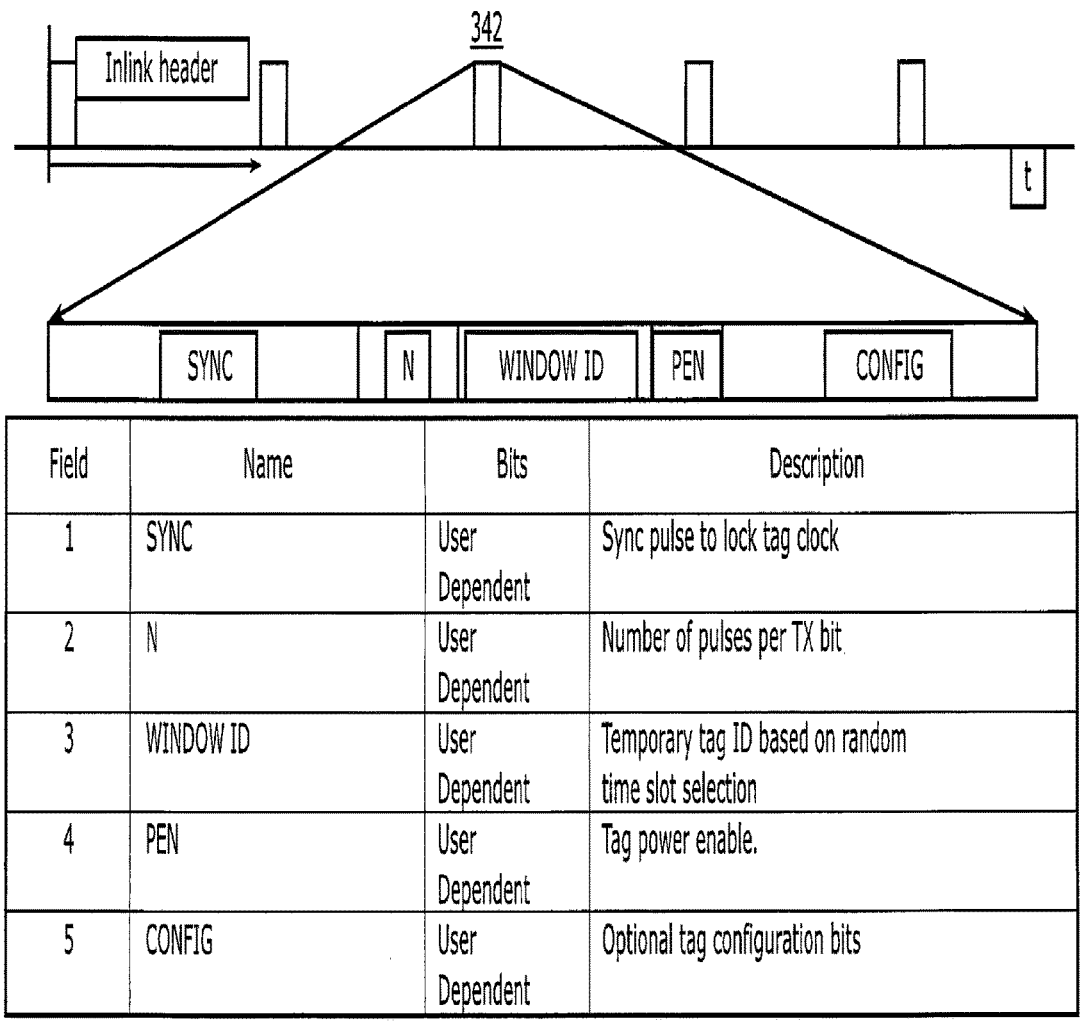
FIG. 16 is a chart depicting the content of the inlink transmission from the reader to the tag.

Referring to FIG. 16, a representative efficient inlink data field 342 and corresponding definitions are shown. Field selection can be used to improve the robustness of the communications between the reader 11 and the tag 15. For example, the field N defines the number of data bursts 332 that the tag 15 uses to define a single tag information bit. Thus, it is appropriate to use a mechanism by which the system 10 assigns more data bursts 332 per bit for situations where the signal to noise ratio may be poor (very large patients for example). This allows for more integration time and improved reliability. Such a system is adaptable for broader utility.

Figure 17:
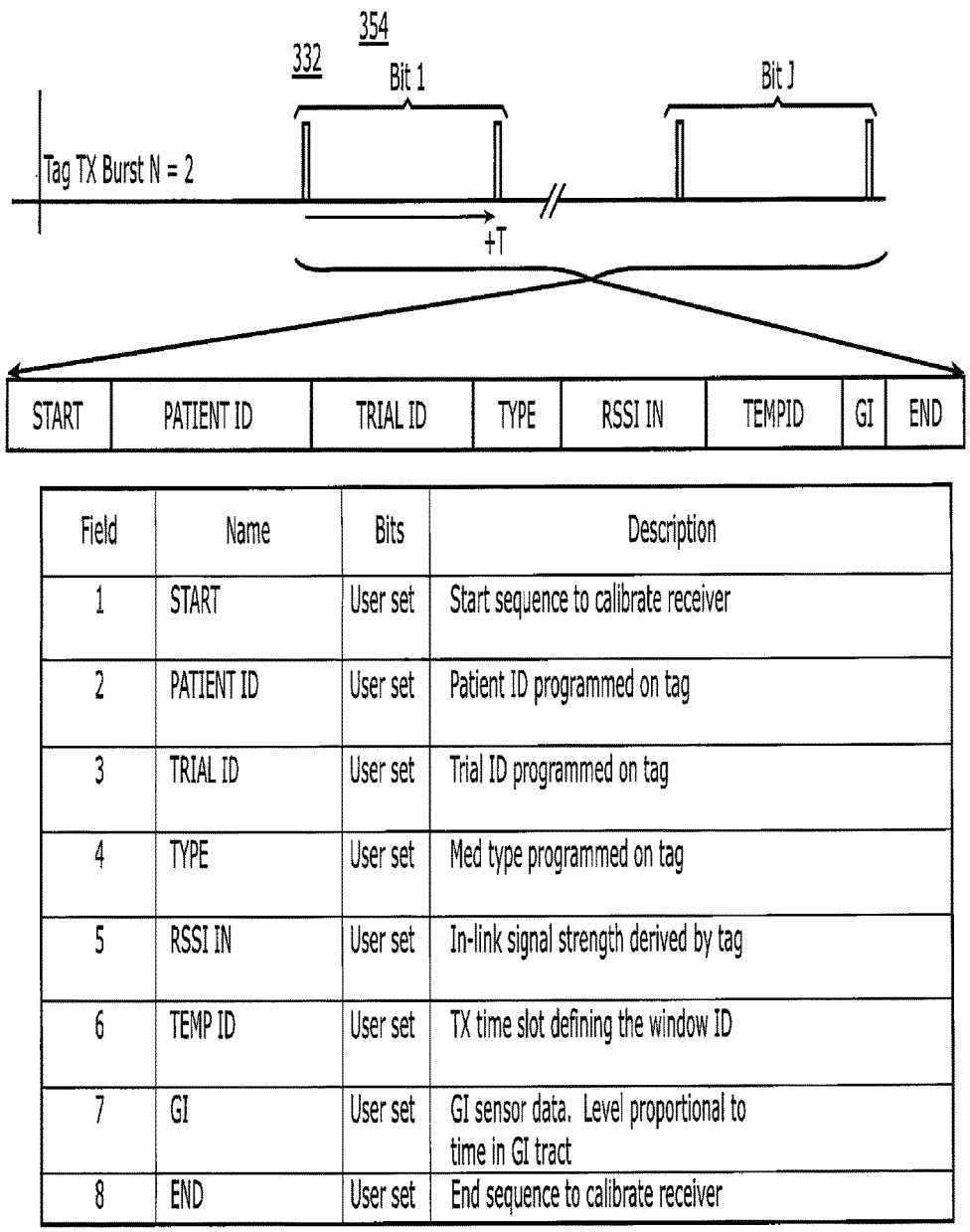
FIG. 17 is a chart depicting the content of information contained in the data bursts from the tag to the reader.

Referring to FIG. 17, a representative efficient outlink data field 352 is configured to allot two data bursts 332 for a single bit 354. Depending on the total number of bits J of information transmitted, N×J data bursts are generated. For example, if the total number of bits 354 is J=16 and N=2, then 32 data bursts 332 are transmitted. As a further example of the utility of this protocol, the reader 11 may be preprogrammed to only accept outlink data with the proper patient ID. This along with the fact that the data is coherently linked to the reader 11 essentially reduces the likelihood of data not associated with this patient 16 being received as valid data.

Figure 18:
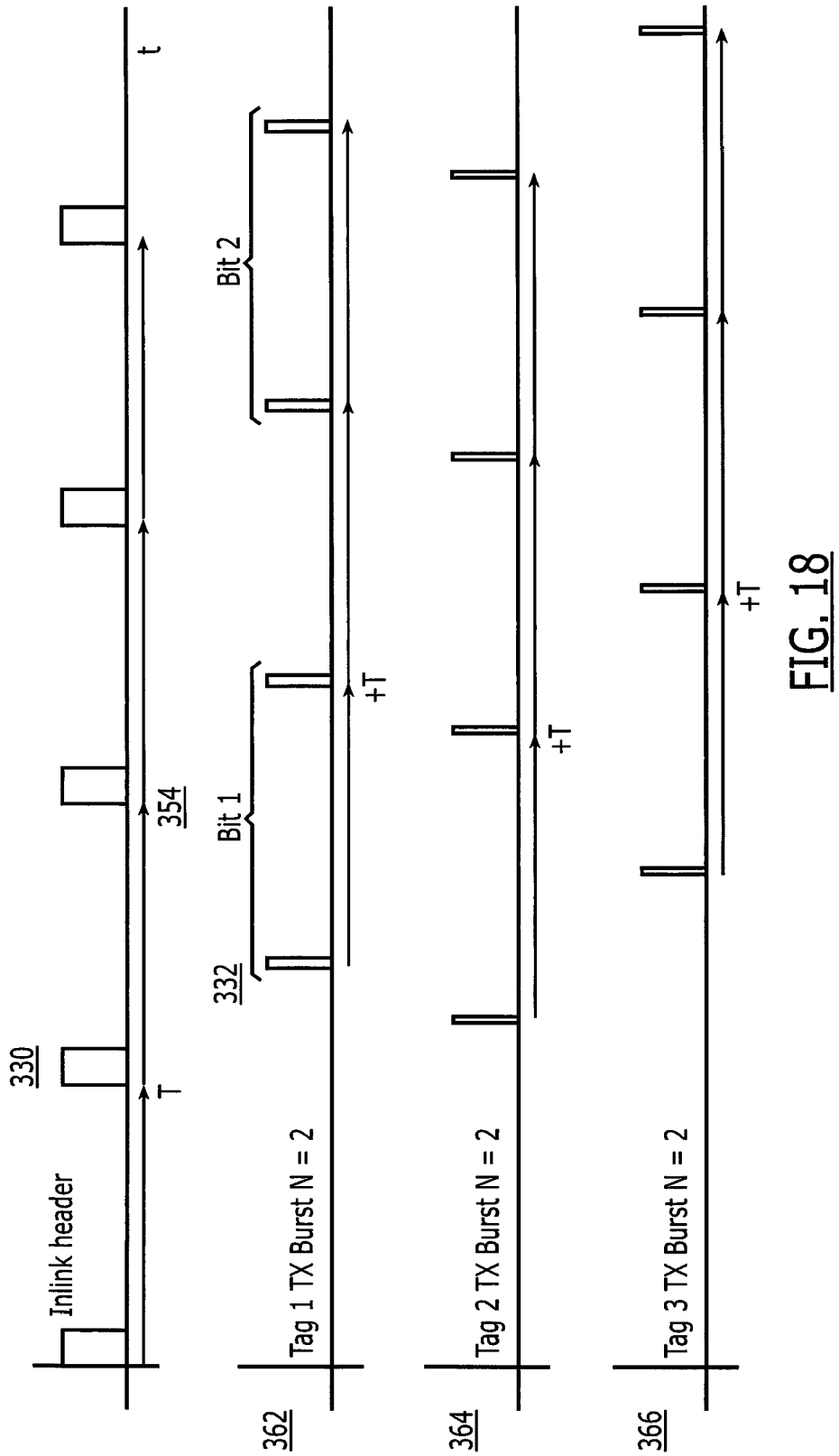
FIG. 18 depicts a timing chart for uplink transmissions from multiple tags to the reader.

FIG. 18 shows the timing for the case of three tags taken together to further illustrate the efficiency of the protocol. Tag 1 362 transmits at a random slot after the inlink header 330 and transmits multiple bursts 332 per bit 354. Similarly, Tag 2 364 and Tag 3 366 transmit their multiburst per bit transmission in different time slots after the inlink header 330.

As has been previously discussed, a communication network utilizing a phase based modulation scheme is known to have advantages of reduced bit error rate (BER) for the same transmission power compared to simple modulation schemes such as Amplitude Shift Keying (ASK). Since power is extremely limited in in-vivo communication systems, minimizing BER is a challenge. Implementing a phase-based modulation scheme requires that the reader 11 be able to coherently demodulate the signal 52 for each tag 15. This normally requires that the frequency stability of each tag 15 be within a tight tolerance (20-40 ppm) to permit the reader 11 to phase lock and demodulate the received signal. Such frequency tolerance requires that the tag 15 transmit frequency be based on a crystal reference. Size and safety constraints prohibit the use of crystals to generate the transmit signal for the tag 15. Further, since the tag transmission burst is short in duration, there may be issues in proper settling which may cause demodulation errors. Another solution is for the reader 11 to have an independent receiver for each tag 15 and preferably use a phase lock loop based approach to lock to the incoming signal. There are issues with this approach as well. First, the burst durations are short making the design of such a receiver extremely difficult. Second, the tag 15 still requires some measure of frequency tolerance to assure regulatory or system specifications are achieved. This may require the need for tag frequency trimming which adds to the manufacturing and test costs of each tag 15. Hence, a method is required to eliminate the need for a tight frequency tolerance on the tag 15 as well as a complex reader 11 receiver design.

Figure 19:
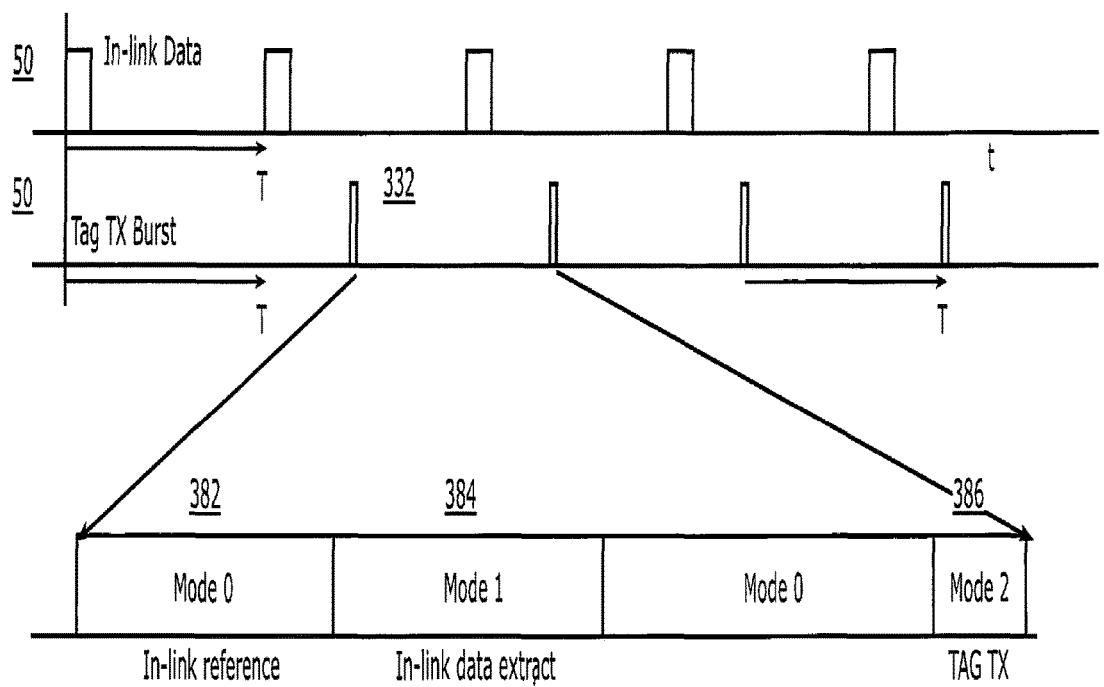
FIG. 19 is a further block diagram of the overall system, illustrating a specific example of conductive transmissions from the reader to the tag at 4 MHz and radiative outlink transmissions from the tag to the reader at 400 MHz by way of example.

A preferred approach takes advantage of the fact that the reader 11 is connected via the conductive inlink 50 communication channel to each tag 15. Hence, by using the reader 11 as the initial frequency reference and locking each tag 15 to the reference signal for reader 11, a self-synchronized coherent communication system is realized. FIG. 19 illustrates this concept in detail. First, the reader 11 generates a reference signal (shown here for example with frequency of 4 MHz). This signal is passed to the conductive channel 50 through an interface circuit 372 and propagated to any tag 15 within the channel. At the same time, the 4 MHz reference 376 is frequency multiplied within the reader 11 to the tag 15 burst frequency (400 MHz by way of example). This signal is ultimately used to coherently demodulate data from any tag 15. In the tag 15, the 4 MHz reference frequency is extracted, amplified and passed to the input of a PLL demodulator and TX carrier generation circuit (TAG PLL) 374. This circuit has several modes of operation including the tag burst mode. During the tag burst mode, the signal is frequency multiplied to the TX frequency of 400 MHz. This signal is subsequently passed through the outlink 52 channel where it is extracted at the reader 11. The reader local oscillator 378 derived from the original 4 MHz reference is used to demodulate the received tag signal 52. The system is self coherent. Thus, the tag 15 achieves a tight transmission frequency tolerance by virtue of the phase lock loop 374 and does not require any internal crystal reference.

Figure 20:
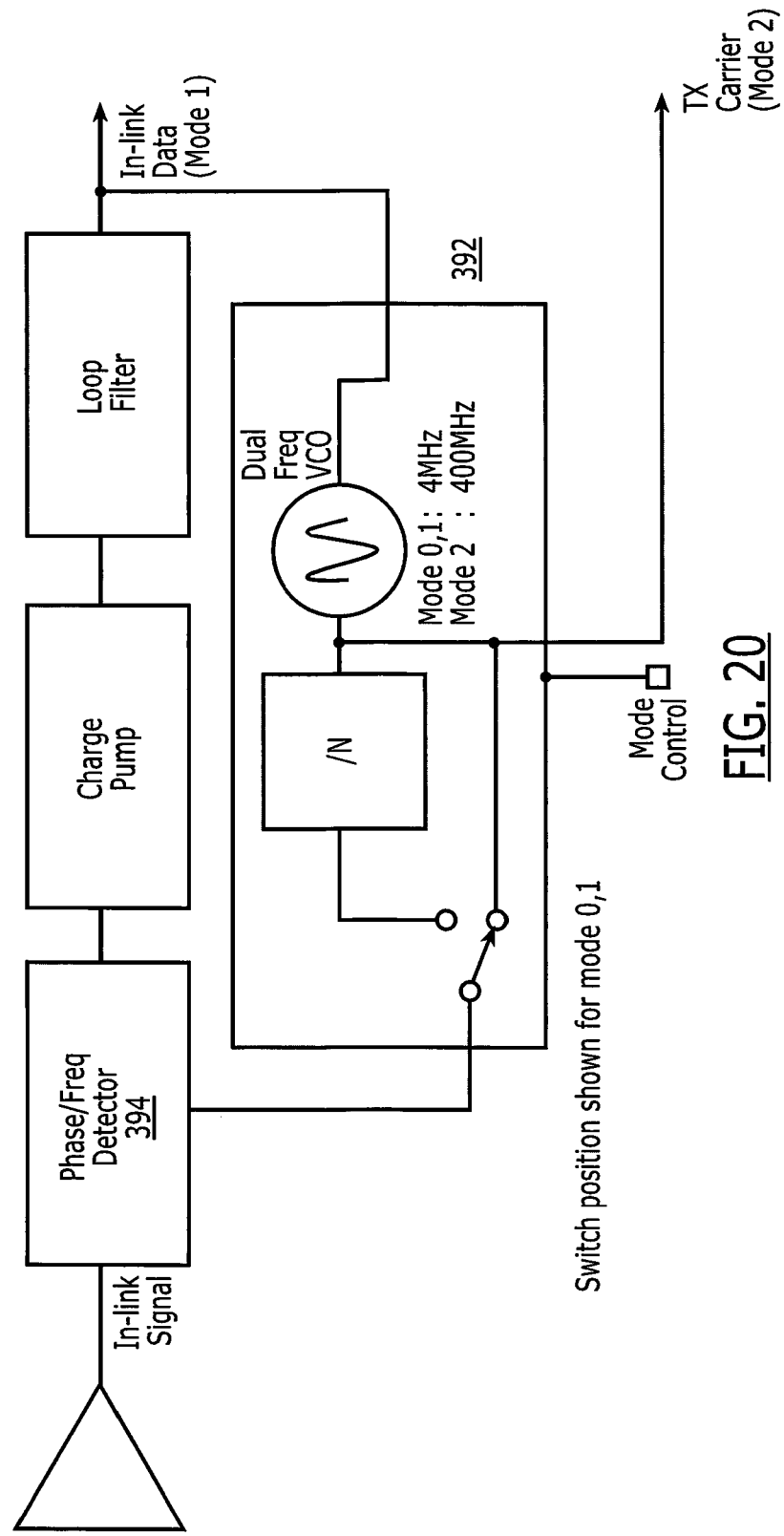
FIG. 20 is another timing diagram illustrating the operation of the system of the present invention.

Other advantages of this embodiment may be seen by referring to FIG. 20. This figure shows the timing relationship between the inlink 50 and outlink 52 burst signal and defines the three modes of operation of the TAG PLL 374 network. The inlink data is sent at a periodic rate of T seconds, typically on the order of 1 ms. As described earlier, the tag 15 responds some time later (less than 1 ms) with a TX burst. The TX burst also repeats at the same 1 ms interval. A single period is expanded in FIG. 20 to further highlight the modes of operation of the TAG PLL. The TAG PLL operates continuously. During mode 0 382, the reader sends a fixed reference signal of frequency Fref (4 MHz). The TAG PLL locks to this frequency and remains locked until progressing to mode 1 384. During mode 1, the TAG PLL remains locked; also during mode 1, the reader 11 frequency modulates the 4 MHz reference signal with any required information or configuration data for the tag 15. Since the TAG PLL is still locked to the reader signal, the modulated data can directly be extracted from the VCO control voltage 375 on the TAG PLL. Hence, during mode 1 384, the TAG PLL is acting as a demodulation block. The TAG PLL then returns to mode 0 382 and stabilizes. Finally, during mode 2 386, the PLL is given the command to frequency multiply the 4 MHz reference signal, generating the 400 MHz TX burst signal. This is an efficient realization using the same circuitry for both inlink demodulation and TX carrier generation.

Figure 21A:
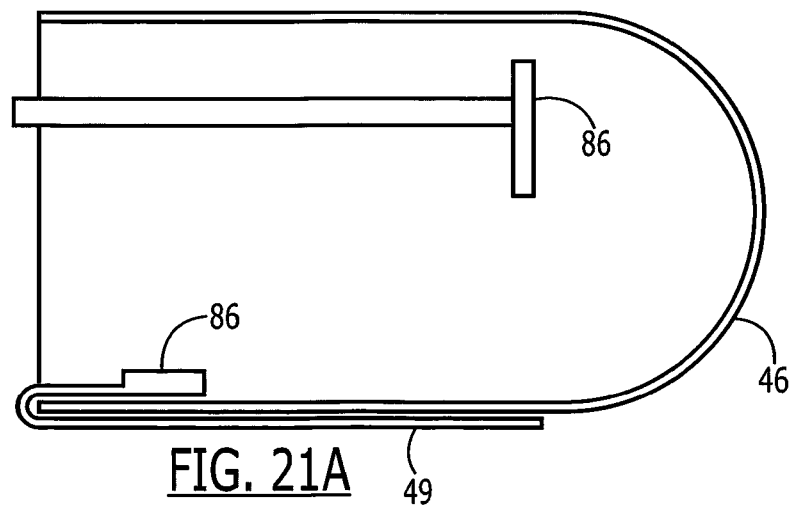
FIGS. 21A and 21B are block diagrams illustrating further aspects of the operation of the system.
Figure 21B:
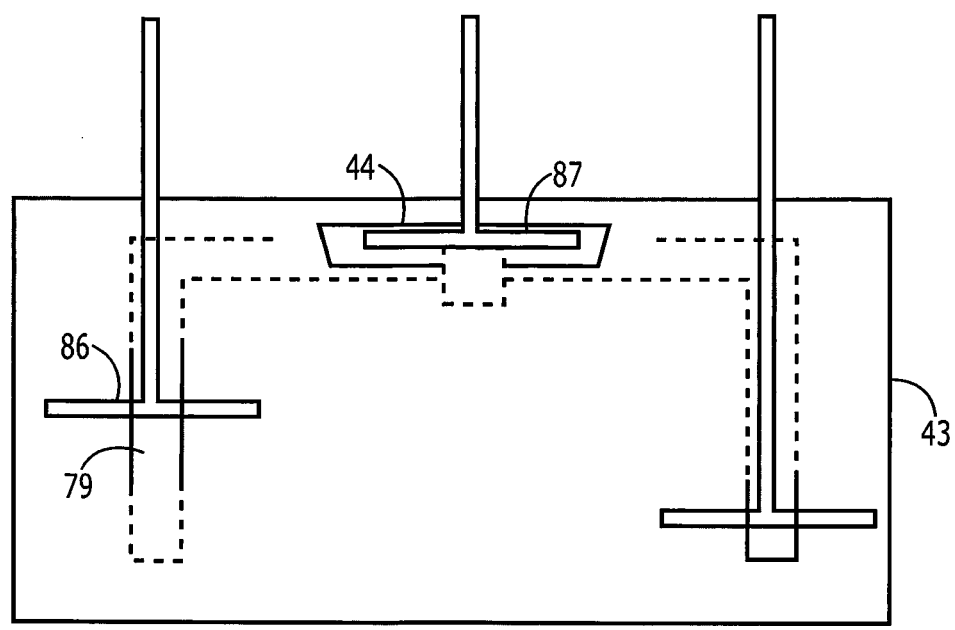

FIG. 21 shows more detail of the TAG PLL 374. One key to its operation is the dual frequency VCO 392. During modes 0 and 1, the VCO 392 operates at 4 MHz. During mode 2 the VCO 392 is switched to 400 MHz (with VCO gain parameters changed accordingly) at the same time a divide by N (100 for this example) is enabled within the loop. The frequency of the phase detector 394 remains unchanged and the loop dynamics remain the same. As a result the loop quickly settles to a precise 400 MHz and the TX burst is transmitted. Once the TX burst 332 is sent, the PLL 374 is returned to mode 0 and the process repeats.

It will be appreciated by those skilled in the art that this implementation has several advantages. Using fine lithography integrated circuit technology, the power requirements for the VCO 392 during mode 0 and 1 are very minimal. Simple ring oscillator approaches may be used for the VCO 392 requiring just a few micro-amps of current. This allows the TAG PLL 374 to operate continuously which then permits a very frequency tolerant transmission burst. The TAG PLL 374 will stabilize with each subsequent burst. The same circuitry is used for both transmit and receive and area requirements are very small leading to a low cost solution. Attachment (Inside, Outside, Both; Premade Built in, Attached)

Wrapped tag embodiments are shown in FIGS. 5A and 5B. Noting FIG. 5B, the wrapping process is typically partially around or completely around the outer surface of capsule 46, soft gelcap, or other medication carrying device as shown in FIG. 5B. The resent invention also includes the method of attaching the tag 43 to the inside surface of the capsule 46 as shown in FIG. 5A.

Referring again to FIG. 5B, to avoid the accidental or purposeful removal of the tag 43 from the outside of the capsule 46, avoid damage to the tag from handling and environmental issues and to increase the aesthetic appeal of capsules (and minimize patient hesitation in taking an electronically-tagged medication), it is prudent to conceal all electronic devices, including antenna 44 and chip 47, inside an opaque or mostly opaque gelatin capsule while maintaining communications to various body-dependent sensors or electronic devices. Inconspicuous leads that lay flat on the surface of the gelatin capsule 46 are likely to be of little indication of the presence of a more complex antenna-chip structure within the capsule 46.

Figure 22:
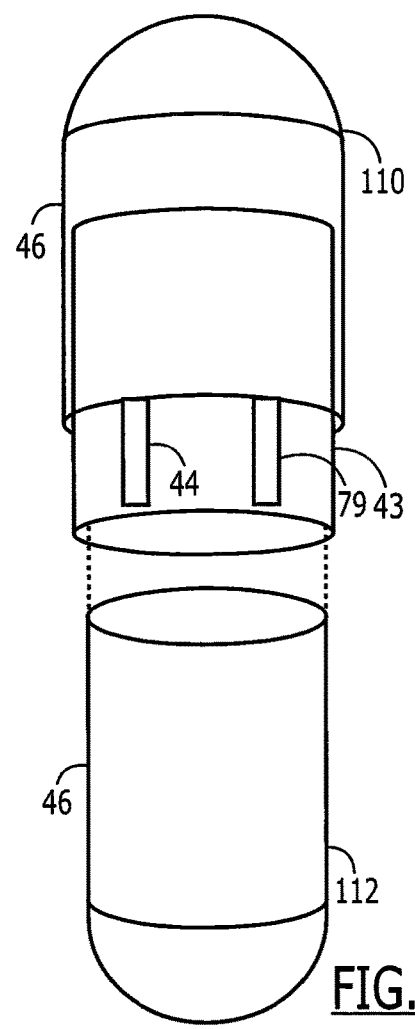
FIG. 22 is a side view illustrating an alternate construction for the electronic capsule to permit a portion of the electronics to be carried within the capsule.
Figure 23:
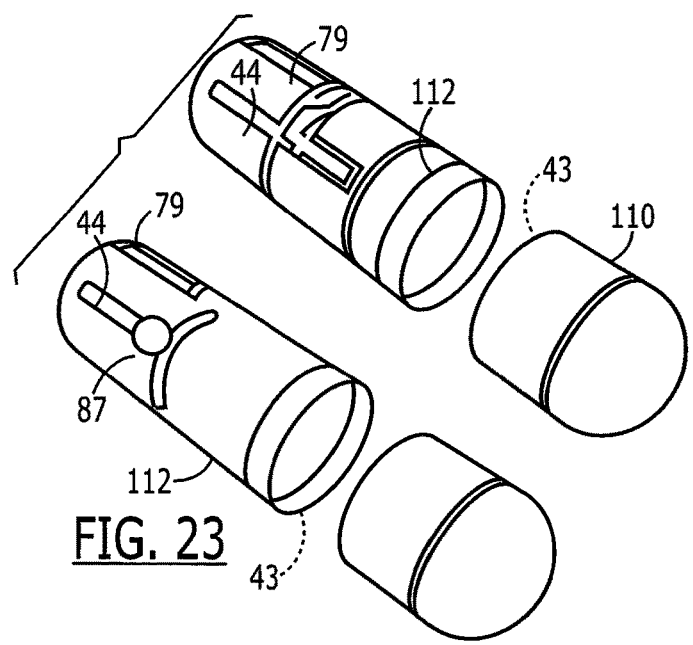
FIG. 23 is an exploded illustration depicting, from left to right, the attachment of an integrated circuit chip to the tag connected to the low frequency and high frequency antenna areas, and the wrapping of the tag about a capsule (right hand side).

Now noting FIG. 5A, further placing the tag 43 inside the capsule 46 maintains a minimal change in capsule volume, and simplifies tag attachment and functionality. Referring to FIGS. 22 and 23, a trace or foil 49 that runs from inside the gelatin capsule to its exterior allows for electronic transmission from within a capsule or power harvesting from outside the capsule. The exposed antennas or leads 79, 44, 81 on the tag 43 make electrical contact with the interior-exterior lead 49 on the capsule 43. The interior-exterior lead 49 is preferably constructed such that an elongated pads 86, 87 are included to make contact with the antennas or leads 79, 44, 81 of the tag 43. The tags are constructed with coatings such that only the leads or antennas that need to be connected to the interior-exterior leads are exposed while all other electrical components and antennas are coated in a protective and/or dielectric substance. To make the interior-exterior connection, the metal film 49 is thin enough to allow a 2-part gelatin capsule to still snap together, The tag 43 itself, being composed only of thin components (antenna, chip, substrate, etc.), takes up a minimal amount of volume within the capsule 46 and should not impair drug loading amounts.

When the pill 14 is in the form of capsule 17, an alternative method is to place the tag 15 inside the capsule and allow the tag to work normally after the capsule begins to absorb fluids. A tag 15 using leads that make contact with the interior wall of the gelatin capsule 17 and activate upon wetting of the capsule can react with the environment to identify location, chemistry, or otherwise. The system 10 can then use the gelatin capsule itself as a protective system in non-aqueous environments. The diffusion time of fluid through the capsule wall is the limiting factor for detection of body fluids or transmission/reception of signal within the body itself. To make contact with the outside environment in an expedient manner, however, the receiving pads must be in direct contact with the capsule as some pills simply swell outwardly. Thus, for this approach an adhesive for attaching the tag 15 to the inside wall of the capsule 17 is required. This will help prevent tampering, prevent misfiring of the pill 14 in beverages or other liquids, or other problems with proper antenna function as there are no external leads whatsoever. Destruction of the pill 14 and its contents is then necessary to access any electronics.

In most cases, placing the tag 15 inside the capsule works well. In some cases, the delay between ingestion and activation of the sensor system on the tag 15 when using a gastro-intestinal powering system may be problematic. Fitting the tag 15 with external exposed sensor or pads would be advantageous for quick analysis of the body environment for advanced location discernment. Transit from mouth to stomach typically takes place in less than 8 seconds, which is faster than most gelatin capsules can absorb fluid and begin to break down. Having an external lead minimizes this delay in sensing time for an internally-placed tag 14. The number of pads that need to be exposed can be as few as one, depending on configuration.

Noting FIG. 23, in one embodiment, the tag 43 has a chip 47 with a high frequency antenna 47 and a low frequency antenna 79, both deposited on a biocompatible substrate 45 that fits inside a gelatin capsule 17. Leads 78 on the antenna 72, 73 are exposed to make contact with the external pads 80 surrounding the capsule 76. This embodiment also allows for "hot-swapping" of internal and external components of the tag 70. Different geometric designs of an external antenna can be accommodated by an internal tag by creating a system that simply needs "lining up" of antennas with external traces. This way, a number of antennas/sensor probes can be produced that have specific applications (frequency, power transmission properties, size, complexity) for a specific drug, creating a modular design that can have certain unique or complex components placed on the exterior of the capsule 17 and maintain a communication pathway. This also prevents the need for adhesive backing for the internal portion of the tag 70 if the elasticity of the substrate 74 provides sufficient rigidity to hold the tag 70 in the proper location. Additionally, the internal tag 70 can be created on a flat substrate as described earlier, but the external portion of the tag may be sufficiently simple to be printed, built-in, or otherwise attached to the outside of the capsule 76. This embodiment also makes the process of creating multi-metal antennas or sensors simpler as only small strips of material need be placed on the outside of the capsule 70.

In another embodiment, the gastric sensor or other leads that are exposed to the outside of the capsule 76 are placed on the surface of the inner half 76A of the capsule, the portion to the capped by the other half 76B. The antenna 72 is then wrapped around the capsule 76, with the exposed antenna leads making contact with the metal extensions on the capsule's inner half 76A (see FIG. 13). In this way, the tag 70 itself is concealed and only two very small metal strips are exposed, improving the appearance of the capsule 76.

Figure 24A:
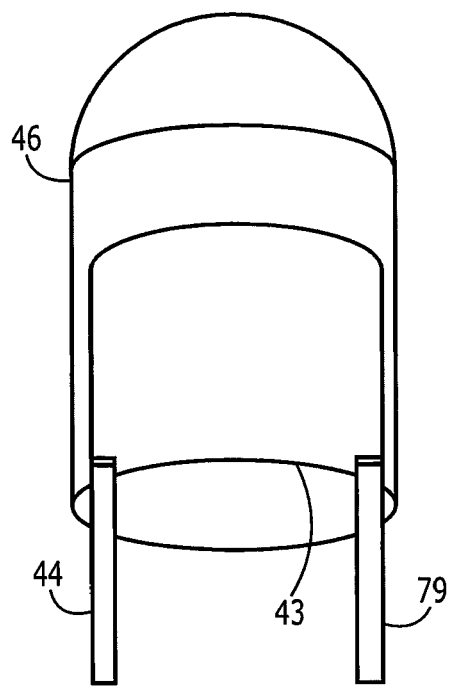
FIGS. 24A and 24B depict exemplary constructions of a capsule with a tag in accordance with this invention.
Figure 24B:
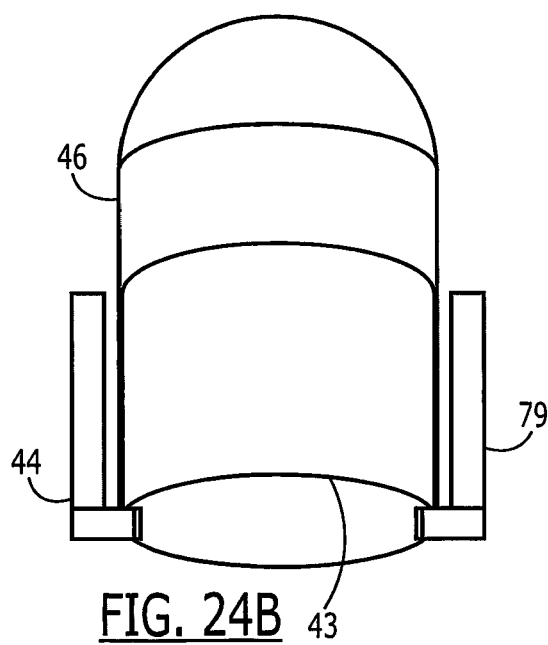

Referring to FIG. 24, the internal component of the tag 43 is inserted into the cap of the capsule and slides over the antennas 44, 79 printed or affixed to the smaller diameter portion of the capsule. When the tag is inserted into the smaller diameter portion of the capsule, via's or through holes 80 are punctured into the capsule to allow connection from inside to outside the capsule when necessary.

Tag Construction

Figure 25:
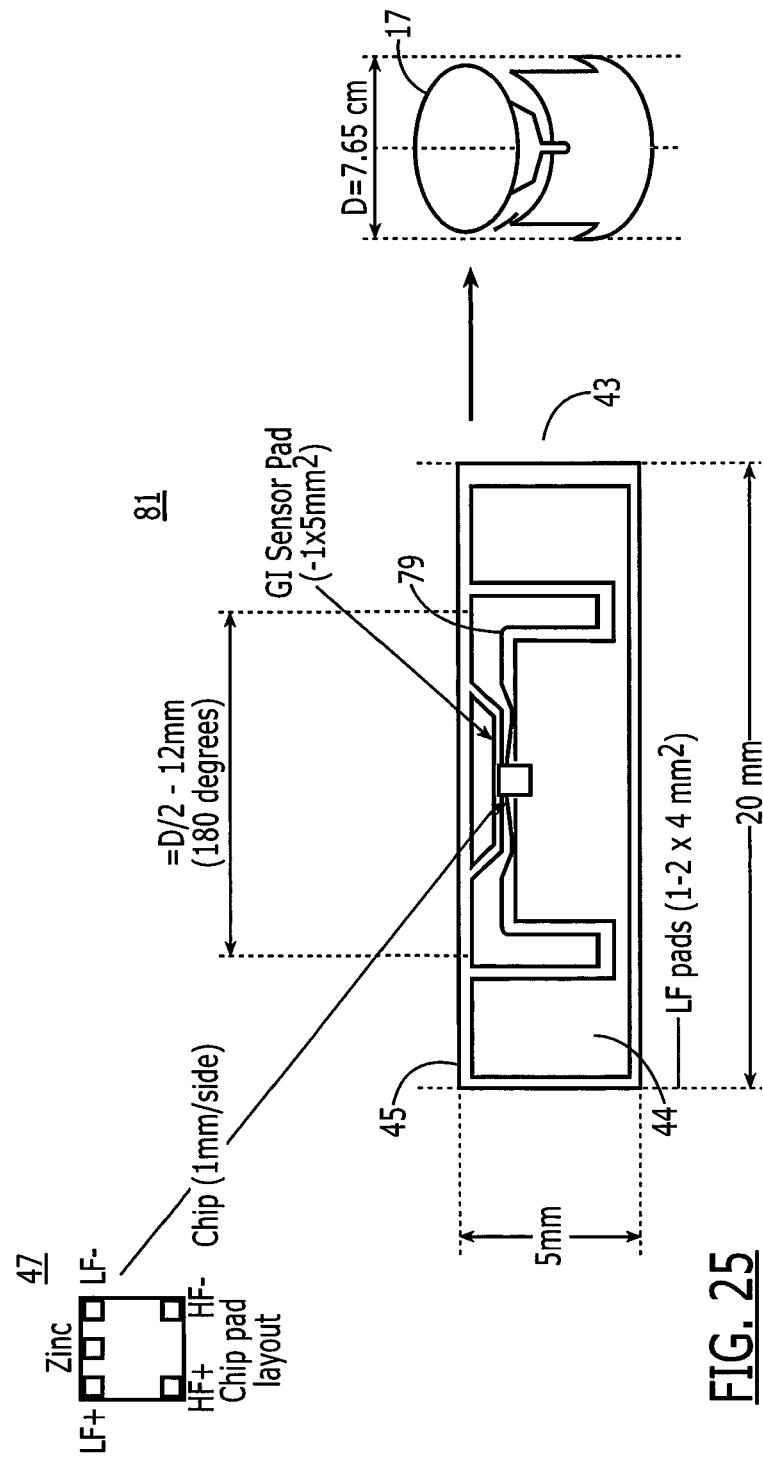
FIG. 25 is a top view of the tag, illustrating various dimensions and small component details and a wrapped configuration.
Figure 26:
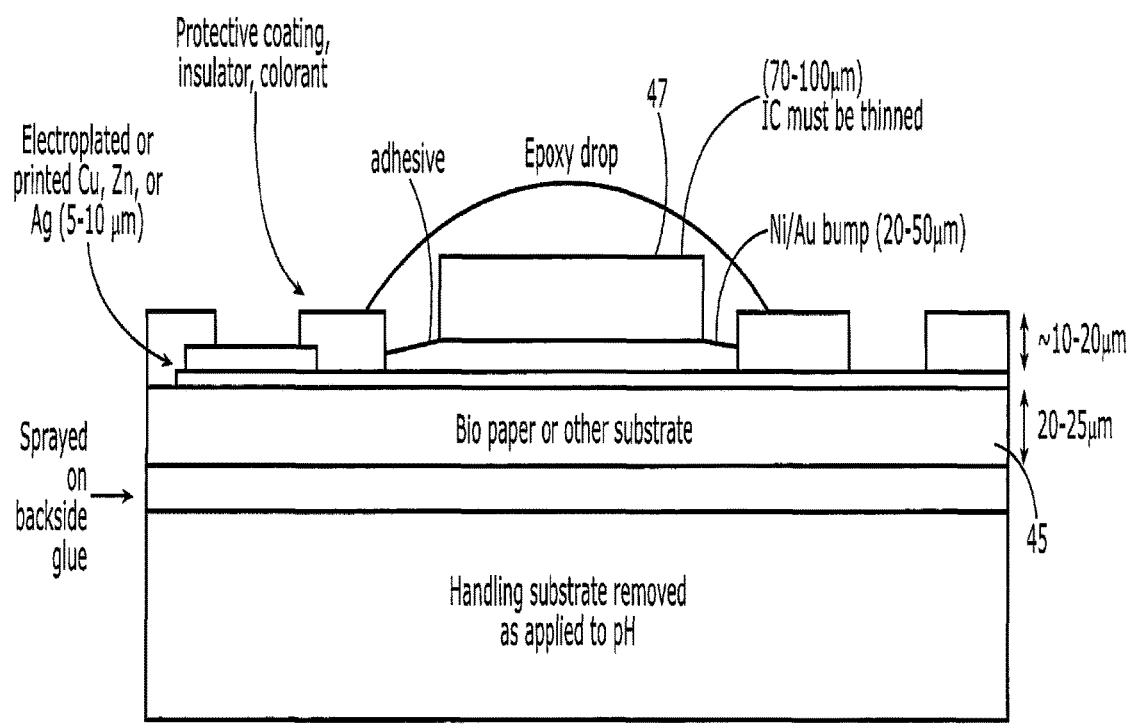
FIG. 26 is a cross-sectional side view of the tag, illustrating various dimensions associated with the elements depicted in schematic form in FIGS. 6A and 6B.
Figure 31:
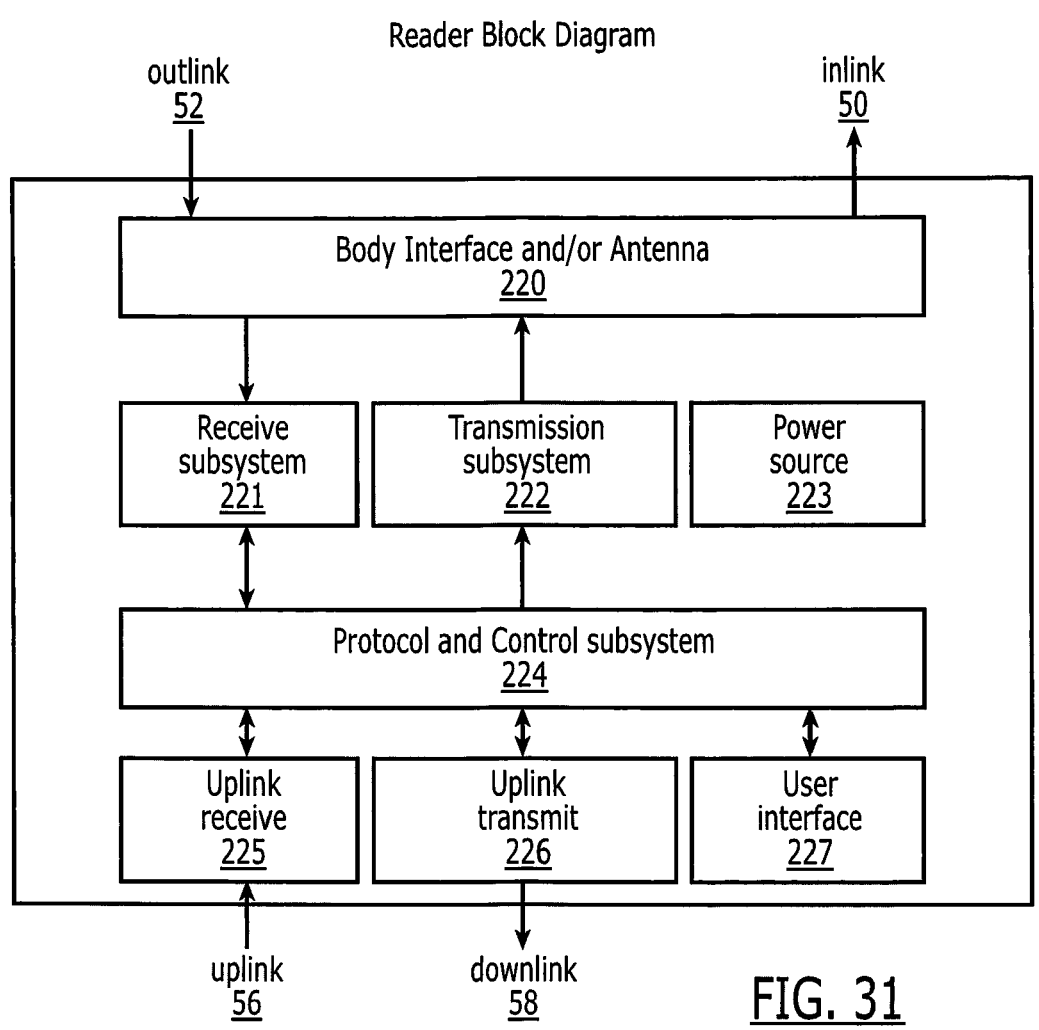
FIG. 31 is a block diagram of the reader 19 in FIG. 1.

Referring to FIGS. 25 and 26, in the preferred embodiment, the main components of the tag 15 are a very small integrated circuit (IC) 71, a metal antenna 72, a gastrointestinal (GI) sensor/energy cell composed of a specially coated GI sensor pad that doubles as an inlink antenna 73 and a second metalic GI sensor pad 75, and a substrate 74.

The substrate 74 is composed of a specially coated paper. Non-whitened, low-weight papers are non-toxic and become softened in the GI tract M, E, S, D, I, R to allow for easy passage without risk of lodging as it passes. These papers will then be coated with a pharmaceutical enteric coating known as "Eudragit", which provides a smooth surface to allow printing of antennas. Eudragit is also a pH-sensitive material that will dissolve in the colon R, allowing the tag 15 to remain active long enough to be detected before disintegrating.

The biocompatible antennas 72, 73 are printed on the substrate and preferentially coated with Eudragit as described above to protect the antenna and prevent interaction with the antenna materials until the tag passes into the colon R where it begins to disintegrate.

The GI sensor/energy cell includes the use of a zinc electrode 75 and silver electrode 73 with special coatings as described previously. The GI sensor is designed to restrict the bioavailability of the materials to levels far below FDA, EPA, and/or recommended daily intakes. The simple GI sensor produces induced voltages from the voltaic battery when different metals interact with the acidic GI fluids. Zinc foil is preferably used for small scale production and is bonded to the tag 15 using a conductive adhesive. An analog to digital converter within data acquisition block 304 in the chip 20 is used to uniquely detect the sensor's response to GI fluid.

FIG. 26 shows the preferred embodiment of the tag, its size, and its approximate location of features. The tag 15 consists of four logical components: the tag body interface 73, the GI sensor 75, the tag integrated circuit (IC) 71, and the out-link TX antenna 77. The tag body interface 73 includes two in-link 50 pads (body contact pads) that are 1-2 mm by 4 mm. The GI sensor includes a pad 75 that is approximately 1 mm×5 mm. The out-link antenna 77 utilizes the rest of the available space. The tag IC 71 is shown in the inlay of the figure. FIG. 26B represents the tag after it is wrapped around a cylindrical object. The in-link antenna pads are separated by the maximum available distance, which is 180 degrees across the capsule once the tag is wrapped around it. The out-link antenna is optimized for the required three dimensional geometry of the capsule (or pill) after attachment. The tag 15 materials and construction conforms to all safety, regulatory, and manufacturing requirements. The physical structure of the tag 15 and its relationship to a medication capsule is shown in FIG. 27. Target Tag sizes are shown such as to conform to a size 0 capsule. Future generations are expected to support smaller capsule geometries and tablets.

Reader

To minimize the size and power requirements of the external reader 11, in one embodiment it may not include the capabilities to transmit information via a cell system, wi-fi, or other wireless network. However, in another embodiment, the reader 11 can transmit data to a standard cell phone, pager, or other device as shown in FIG. 1 and as described below with reference to FIG. 3, to allow for real-time updating of patient compliance and monitoring. Using a two part reader system allows for a miniaturized on-body receiver 19 and a more powerful mobile device 54 with a more sophisticated user interface for messaging and transmission to a global database. In such a two-part reader system, an on-body reader 11 has two communication systems, one 50, 52 to communicate with the tag 15 and one 56, 58 to communicate with the mobile device (for example a bluetooth; see FIGS. 3 and 30 and discussion below). In such a system, the mobile device only requires special software to operate as both a standard mobile device and a front-end user interface and wide area network (WAN) transmission interface.

The external reader 11 can be embodied in several forms. For example, the reader can be the wristband 111 of FIG. 28, or the patch 211 of FIG. 29 that can be adhered to the skin like a bandage, an arm band, a handheld device or the like. In some embodiments, it is advantageous for the reader to have contact with the skin during a medication event. It is also advantageous to design the reader to be readily available and/or worn to ensure it is present with the patient 16 for all medication events. Another form is the pill container 311 shown in FIG. 30 with contacts 313 on the bottle holder 311 for skin contact during the ingestion of the medication. A minimal user interface exists on the bottle holder 311 with a button to indicate ingestion has taken place 312 and an indicator 313 to determine when the pill was detected. The patient 16 removes the medication from the container 311, ingests it, presses button 312 and holds the pill container 311 against the skin until the ingestion event is detected at the contacts 313 and the indicator 314 confirms that the tag 15 was detected in the body 16. In other forms, the reader is also built into a mobile device such as a cell phone, PDA, wrist watch, or into a memory card, dongle, or other add-on device that can be attached or inserted into a mobile unit.

Noting FIG. 30, each reader 11, 111, 211 and 311 has a small user interface 227 that presents indicators of ingested medication being detected and/or the capabilities to indicate when medication should be ingested. The readers are disposable or reusable, or contains portions that are disposable and reusable. The readers also preferably contain means for storing the recorded data for downloading via USB or other means directly to a PC or other computing device. The readers are also preferentially rechargeable. In addition, for those applications where the readers do not need to be mobile, they may be built into a dongle or other means into a standard computer or laptop.

Continuing with FIG. 30, the reader comprises several RF/analog front-end components interconnected with a digital processing core to handle the communication protocols. The body interface or antenna subsystem 220 interfaces with the body 16 or media surrounding the body (e.g., air). It contains the antenna and or contact points to transmit the inlink 50 data to the tag 15 and receive the outlink 52 data from the tag 15. In addition, the body interface subsystem 220 includes the sensors, contacts, or antennas necessary to acquire physiologic or biometric data required to ensure the reader 11 is on the right patient 16 and the tag 15 has been ingested by the right patient. The receive subsystem 221 and transmission subsystem 222 contains the electronics to drive the antennas and/or receive data from the body interface and antenna subsystem 220. The uplink receive 225 and uplink transmit 226 subsystems transmit data to and from an either a mobile device for wide area communication or directly to a wide area communication system such as cell phone, wifi, or paging networks. The protocol and control subsystem 224 manages the communications of the outlink 52, inlink 50, uplink 56, and downlink 58 transmissions, controls the user interface 227 and processes all data coming in and out of the reader 11. The user interface system 227 provides information to the patient about when a tag 15 has been detected, allows the patient 16 to initiate a manual detection, provides indicators of when the pill 14 should be taken, and provides other information to the patient.

The transmission subsystem 220 consists of a multiple modules. The first module contains a high voltage modulator stage with a programmable low frequency carrier to galvanically couple RF signals into the body 16. The supply voltage of the modulator can be dynamically varied to superimpose in-link telemetry data to communicate with the tag on the pill. Digital input signals will be derived from the protocol and control subsystem 224 tasked to handle communication protocols to and from the tag and also to and from an uplink/downlink transceiver 225, 226 that wirelessly interconnects mobile devices to the reader 11. The second module is a UHF receiver chipset used to demodulate out-link 52 data from the tag 15. The receiver is used to downconvert the detected out-link RF signals 52 for data extraction by the baseband processor. Preferably, all communication protocols between reader 11, tag 15 and mobile devices 54 are synchronized to a master clock generation module to ensure proper timing control.

Software System

True adherence improvement is likely to only be achieved when the patient 16 is motivated to follow the prescribed regimen. By connecting the patient with the medication, the pharmacodynamics (PD) and pharmacokinetics (PK), dose/response data, and their own reaction to the medications, patients become more interested in their regimen and become more adherent. The software system is preferentially implemented in a smart phone application that is linked to the reader 11 and the information provided by the uplink/downlink data. In a preferred embodiment, the software shows estimated blood levels of the drug of interest based on the known patient information and medical information stored in the system, as well as the exact timing and doses of the medication taken by the patient. The software shows the patients how missing doses or improperly taking their medication affects their simulated blood levels, drug effectiveness, and how it changes their physical responses to the medication.

Other embodiments include personalized calendars that a list each medication and dosage listed under the following 4 times periods: Morning, Noon, Evening, and Bedtime. If a patient does not take their medicine, they are asked to write the reason. It also lists any special instructions to help prevent adverse effects resulting in decreased medication adherence. The software also contains a list of abbreviated instructions on how to use and monitor each drug so that the patient understands the benefit and risk of each drug. The software also allows the pharmacist to enter how many days late the patient comes to the pharmacy for a refill of chronically taken medication. If the adherence rate is unsatisfactory, the pharmacist is presented with various options on how to enhance adherence through patient education programs designed from well documented motivational interview techniques.

The Personalized Medication Adherence Registry (PMAR) is a mobile software system that receives medication adherence data from the patient and device links, then presents it to the patient and healthcare providers in an extremely quick and easy to understand format. The largest group that will benefit from PMAR are those patients taking multiple chronically administered medications that are essential to wellness. Another important population are patients who are receiving medications that create frequent or severe adverse drug reactions (ADRs). Typical examples of healthcare providers are all physicians, pharmacists, nurse practitioners, physician assistants, clinical trial personnel, and any other health related professions who advise, monitor or treat patients with medications.

When patients visit their physician or other health care providers, they are usually asked to produce a comprehensive, up-to-date, and accurate list of all their medications including the name of the drug, the dosage strength, and the directions for use. This list can become extremely complex very quickly and difficult to recall. This list is immensely valuable when a patient is traveling and in an accident. It may be life saving if this medication list can be produced as quickly as possible with all the required details. Having an electronic copy immediately available can save the patient time and money while improving their health and possibly preventing an inappropriate drug related catastrophe. A common example is when one of over 20 million Americans with diabetes becomes extremely weak in a public place. If he/she has recently taken his blood sugar lowering agent, a liquid with concentrated sugar e.g. a soft drink or orange drink may save their life. The patient must provide their username and password to allow others access to this encrypted information. Since this protected information resides on their cell phone, access to cellular service is not required. A back-up of all this protected information can also be accessed by the patient and any healthcare provider, family member or close friend who has access.

If the patient has access to the Internet via their cell phone or personal computer, they will be able to click a drug from their drug list and be linked to drug-specific information in Wikipedia. They will be reminded to print the information and have it validated for its accuracy and personalized application to their situation based upon various factors that are relevant, e.g., all their existing disease stated, medication list, age, sex, weight, diet, and exercise program.

Medication and Refill Reminders

The Reminder feature of PMAR provides a timely visual and auditory notice to the patient via their mobile phone allowing the customer to be alerted for each of their scheduled medications. PMAR is easily customizable as to each patient's preference as to how they are to be reminded and the sound/vibrate/visual notification rules governing the reminder system. They can reminded to take all their prescription medications (Rx's), OTCs, herbal medications, and nutritional supplements. This information is stored in their cell phone calendar and also does not require access to a cellular network.

PMAR will also remind the patient several days prior to completing their medication that it is time to obtain a new refill or if they are probably almost out of their OTC, herbal, and nutrition supplement. This prevents one of the leading causes of proper medication adherence. These reminders are based upon the date of the last refill and whether they received a weekly, monthly, or quarterly refill.

Although reminder systems are not uncommon, when coupled to compliance monitoring systems, additional features become possible. For example, if medications are not ingested when requested, a series of reminders or alerts can be sent starting with the patient and following up with family, care givers, doctors, pharamcists, drug trial monitors and administrators. If necessary, the system or support personnel can call or visit the patient to ensure that there are no problems and that the patient is taking the medication regularly.

Adverse Drug Reaction Report (ADR)

When the patient is reminded to take their medication, one of their options will be to choose from a list of common side effects and ADRs to document if they have experienced a recent ADR and if they stopped taking their medication secondary to the ADR. This often happens without the pharmacist or physician being aware. This will assist healthcare providers in determining the cause of patient non-adherence and prompt them to possibly decrease the dose or select an alternative medication. This feature alone can help decrease many avoidable hospitalizations.

Other Features

Referring again to FIG. 1, as an alternate to detection of the pill in the gastrointestinal system, it is also possible to detect a pill 30 as it passes through the esophagus E using a sensor 32 designed to fit around the neck 33. Preferably, this sensor 32 takes the form of a complete circle around the neck 33, a partial, horseshoe-like enclosure, or a simple device held against the neck 33. The sensor 32 detects all embodiments of the pill 30 described elsewhere as it passes through the esophagus E into the stomach S. The embodiments in which the sensor 32 forms a semi- or full circle around the neck 33 also improve the signal-to-noise ratio over a sensor that is simply held in front of the patient. There is also less dependence on digestive mechanisms, providing less design restrictions on the pill itself.

The neck sensor operates in all the same ways as the gastrointestinal reader 11, but also allows for other, possibly advantageous, protocols. For the case in which multiple pills must be detected, a protocol in which the patient takes one pill at a time can be employed. In this approach, only one pill will occupy the esophagus E at any time, which improves the sensor's capability to identify and tally dosage.

The above specification and the drawings have been used to disclose a number of embodiments of this invention. Specific terms have been used in a descriptive sense only and not for purposes of limitations. It will be appreciated by those skilled in the art that various changes and modifications can be made in the above described embodiments without departing from the spirit and scope of this invention.

What is claimed:

1. An electronic system for monitoring a patient's ingestion of an ingestible delivery device, the electronic system comprising:
   an ingestible delivery device;
   an electronic circuit associated with the ingestible delivery device and configured to generate and transmit one or more radio frequency signals to indicate the ingestion of the delivery device; and
   an electronic reader positioned externally to the patient and configured to receive one or more radio frequency signals from the electronic circuit.

2. The electronic system of claim 1, further comprising at least one remote device configured to receive information from the electronic reader and generate data indicative of the patient's ingestion of the delivery device based at least on the information received from the electronic reader.

3. The electronic system of claim 2, wherein the at least one remote device is further configured to upload the data indicative of the patient's ingestion of the delivery device in at least one remote database.

4. The electronic system of claim 1, wherein the electronic circuit is configured to generate the one or more radio frequency signals in accordance with a plurality of programmable data fields, wherein at least a portion of the plurality of programmable data fields are configured to facilitate at least the electronic reader to detect the presence of the delivery device within the patient's body.

5. The electronic system of claim 1, wherein the delivery device is associated with a unique identifier, and the electronic circuit is configured to transmit data representing the unique identifier to the electronic reader.

6. The electronic system of claim 5, wherein the electronic reader is configured to receive and differentiate radio frequency signals from multiple electronic circuits that are within the patient's body and are simultaneously communicating with the electronic reader.

7. The electronic system of claim 1, wherein the delivery device contains one or more medicines.

8. An ingestible electronic system for tracking ingested medication in a patient's body, the ingestible electronic system comprising:
an electrically insulated substrate;
an electronic circuit fitted to the substrate and configured to generate and transmit one or more signals in accordance with a plurality of programmable data fields, wherein at least a portion of the plurality of programmable data fields are configured to facilitate at least a detection of a status of the delivery device within the patient's body; and
an antenna disposed across the substrate and electrically coupled to the electronic circuit for transmitting the one or more signals.

9. The ingestible electronic system of claim 8, wherein the substrate comprises multiple layers of coatings for tracking the substrate when the substrate is exposed to different solutions in the patient's body.

10. The ingestible electronic system of claim 8, further comprising a plurality of sensors coupled with the electronic circuit, wherein at least one sensor of the plurality of sensors is configured to provide varying inputs to the electronic circuit dependent upon a location of the at least one sensor in the patient's body.

11. The ingestible electronic system of claim 8, wherein the electronic circuit is configured to transmit the one or more signals to an electronic reader positioned externally to the patient's body.

12. The ingestible electronic system of claim 11, wherein the electronic reader comprises a first subsystem for communicating data with the electronic circuit, and a second subsystem for communicating data with at least one remote device.

13. A method for monitoring a patient's compliance with a medication program, the method comprising:
positioning an electronic reader externally to a patient;
providing to a patient a medicine delivery device comprising an electronic circuit;
having the patient ingest the medicine delivery device;
transmitting, by the electronic circuit to the electronic reader, one or more radio frequency signals that are generated after the patient ingests the medicine delivery device; and
connecting at least one remote device to the electronic reader, wherein the at least one remote device is configured to receive the one or more radio frequency signals from the electronic reader and generate data indicative of the patient's compliance with the medication program based at least on the one or more radio frequency signals.

14. The method of claim 13, wherein the one or more radio frequency signals are generated in accordance with a plurality of programmable data fields, wherein at least a portion of the plurality of programmable data fields are configured to facilitate at least the electronic reader to detect the presence of the medicine delivery device within the patient's body.

15. The method of claim 13, further comprising:
associating a unique identifier with the medicine delivery device; and
transmitting, by the electronic circuit, data representing the unique identifier of the tag to the electronic reader.

16. The method of claim15, further comprising:
receiving and differentiating, by the electronic reader, multiple radio frequency signals from multiple electronic circuits that are within the patient's body and are simultaneously communicating with the electronic reader.

17. The method of claim 13, wherein the electronic reader comprises a handheld mobile device that is positioned externally to the patient.

18. A non-transitory computer-readable medium having one or more instructions which, when executed by one or more processors of a computing device, causes the one or more processors to perform operations comprising:
receiving, by the computing device, information relating to a medicine delivery device from an electronic reader positioned externally to a patient within a distance after the patient ingests the medicine delivery device, the medicine delivery device comprising an electronic circuit, the electronic circuit being configured to transmit the information relating to the medicine delivery device to the electronic reader while the electronic circuit being exposed to different solutions inside the patient's body;
uploading the information relating to the medicine delivery device in real-time to at least one remote database;
receiving drug specific and patient specific information from various sources;
generating data indicative of the patient's compliance with a medication program based at least on the information relating to the medicine delivery device and the drug specific and patient specific information; and
presenting the data to the patient.

19. The non-transitory computer-readable medium of claim 18, wherein the at least one remote database is accessible by at least one of a healthcare provider, physician, clinical trial personnel, family member of the patient, pharmacist, or insurance company.

20. The non-transitory computer-readable medium of claim 18, wherein the data presented to the patient comprise a list of common side effects and adverse drug reactions for the patient.

* * * * *